US012617740B2

(12) United States Patent
Curren et al.

(10) Patent No.: US 12,617,740 B2
(45) Date of Patent: May 5, 2026

(54) FRACTIONATION FOR POLYMERIZED REACTOR EFFLUENT

(71) Applicant: Chevron Phillips Chemical Company LP, The Woodlands, TX (US)

(72) Inventors: Joseph A. Curren, The Woodlands, TX (US); Wei Qi, The Woodlands, TX (US); Anurag Gupta, The Woodlands, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 226 days.

(21) Appl. No.: 18/437,762

(22) Filed: Feb. 9, 2024

(65) Prior Publication Data

US 2025/0257021 A1     Aug. 14, 2025

(51) Int. Cl.
| | |
|---|---|
| *C07C 7/00* | (2006.01) |
| *B01D 3/14* | (2006.01) |
| *B01D 3/32* | (2006.01) |
| *B01J 19/24* | (2006.01) |
| *C07C 7/04* | (2006.01) |

(52) U.S. Cl.
CPC .............. *C07C 7/005* (2013.01); *B01D 3/148* (2013.01); *B01D 3/322* (2013.01); *B01J 19/2465* (2013.01); *C07C 7/04* (2013.01)

(58) Field of Classification Search
CPC ........ B01D 3/148; B01D 3/322; C07C 7/005; C07C 7/04; B01J 19/2465
See application file for complete search history.

(56) References Cited

U.S. PATENT DOCUMENTS

| | | | |
|---|---|---|---|
| 3,152,872 A | 10/1964 | Scoggin | |
| 3,248,179 A | 4/1966 | Norwood | |
| 4,501,885 A | 2/1985 | Sherk | |
| 4,588,790 A | 5/1986 | Jenkins, III | |
| 4,589,957 A * | 5/1986 | Sherk ........................ | C07C 7/04 |
| | | | 203/99 |
| 5,183,866 A | 2/1993 | Hottovy | |
| 5,207,929 A | 5/1993 | Sung | |

(Continued)

OTHER PUBLICATIONS

International Search Report and Written Opinion dated Apr. 28, 2025 of related Application No. PCT/US2025/013802 filed Jan. 30, 2025, 10 pages.

*Primary Examiner* — Jonathan Miller
(74) *Attorney, Agent, or Firm* — Conley Rose, P.C.

(57) ABSTRACT

A method including recovering a polymerization reactor effluent stream from one or more polymerization reactors, flashing the polymerization reactor effluent stream to form a flash gas stream, separating, in a first column, the flash gas stream into a first column overhead stream, a first column side stream, and a first column bottoms stream, separating the first column overhead stream into a gas stream and a liquid stream, and introducing a feed comprising the gas stream and at least a portion of the liquid stream to a second column to produce a second column overhead stream, a second column side stream, and a second column bottoms stream. A second column bottoms stream flow rate can comprise less than or equal to about 25 vol % of a total flow rate and a second column side stream flow rate can comprise greater than or equal to about 75 vol % the total flow rate.

20 Claims, 8 Drawing Sheets

(56)        References Cited

U.S. PATENT DOCUMENTS

| | | | |
|---|---|---|---|
| 5,322,927 A * | 6/1994 | Ramachandran | C08F 10/00 |
| | | | 585/851 |
| 5,352,749 A | 10/1994 | DeChellis | |
| 5,436,304 A | 7/1995 | Griffin | |
| 5,455,314 A | 10/1995 | Burns | |
| 5,565,175 A | 10/1996 | Hottovy | |
| 5,575,979 A | 11/1996 | Hanson | |
| 6,045,661 A * | 4/2000 | Kreischer | B01D 3/06 |
| | | | 526/348 |
| 6,239,235 B1 | 5/2001 | Hottovy | |
| 6,262,191 B1 | 7/2001 | Hottovy | |
| 6,833,415 B2 | 12/2004 | Kendrick | |
| 7,619,047 B2 | 11/2009 | Yang | |
| 8,492,492 B2 * | 7/2013 | Mills | B01J 19/242 |
| | | | 526/89 |
| 9,096,694 B1 * | 8/2015 | Gupta | C08F 2/01 |
| 9,108,891 B1 * | 8/2015 | Ji | C07C 7/13 |
| 9,394,383 B2 * | 7/2016 | Gupta | B01J 19/245 |
| 10,781,273 B2 * | 9/2020 | Curren | B01J 8/1863 |
| 2006/0094590 A1 | 5/2006 | McDaniel | |
| 2007/0197374 A1 | 8/2007 | Yang | |
| 2009/0004417 A1 | 1/2009 | Follestad | |
| 2010/0029872 A1 | 2/2010 | Jensen | |
| 2010/0041842 A1 | 2/2010 | Yang | |
| 2015/0203601 A1 * | 7/2015 | Gupta | B01J 19/245 |
| | | | 422/132 |
| 2021/0032380 A1 * | 2/2021 | Curren | C08F 10/02 |

* cited by examiner

FRACTIONATION FOR POLYMERIZED REACTOR EFFLUENT

CROSS-REFERENCE TO RELATED APPLICATIONS

None.

STATEMENT REGARDING FEDERALLY SPONSORED RESEARCH OR DEVELOPMENT

Not applicable.

TECHNICAL FIELD

The present disclosure relates to systems and methods for processing an effluent from a polymerization reaction process. More particularly, the disclosure relates to removing one or more undesired components and recycling one or more reusable components from a polymerization reaction effluent stream. Still more particularly, the current disclosure relates to systems and method for treating a polymerization reactor effluent that operates a deethanizer column at a pressure similar to a pressure of an upstream dehexanizer column, with a majority of the isobutane recovered via the deethanizer removed via a side stream of the deethanizer.

BACKGROUND

The production of polymers such as polyethylene requires a high purity feedstock of various components, including monomers, diluents, and co-monomers. In order to offset some of the costs and maximize production, it can be useful to reclaim and/or recycle some feedstock components from an effluent stream resulting from the polymerization reaction. To accomplish this, the reclaimed effluent streams have conventionally either been routed through a purification process or redirected through other redundant processing steps.

Conventional attempts to industrially produce high purity feedstock components has required the operation of numerous distillation columns, compressors (e.g., to achieve the high pressures needed in such conventional processes), refrigeration units (e.g., to achieve cryogenic temperatures) and various other equipment. As such, the equipment and energy costs associated with feedstock purification represent a significant proportion of the total cost for the production of such polymers. Further, the infrastructure required for producing, maintaining, and recycling high purity feedstock represents a significant portion of the associated cost.

Further, such conventional attempts to recover feedstock components have not enabled sufficient control parameters to prevent and/or control deleterious plant conditions. The drawbacks of these designs can lead to process delays, increased costs, and/or other inefficiencies. As such, an improved separation system for polymerization reaction effluent streams is needed.

BRIEF DESCRIPTION OF THE DRAWINGS

The detailed description will reference the drawings briefly described below, wherein like reference numerals represent like parts, unless otherwise indicated.

DETAILED DESCRIPTION

Herein disclosed are systems and methods of treating a polymerization reactor(s) effluent stream. In the conventional flash gas treatment processes, a deethanizer column is operated at approximately double the pressure of an upstream dehexanizer column. This change in pressure requires the inclusion of a dehexanizer overhead compressor. This compressor increases the capital cost of such conventional designs, and can present operational difficulties. Furthermore, operating the deethanizer at higher pressures increases the energy consumption of the stripping process occurring therein. Via the system and method of this disclosure, the deethanizer can be operated at a lower pressure, similar to that of the dehexanizer column, such that the dehexanizer compressor can be eliminated. This can also substantially reduce steam/energy consumption and reduce venting of ethylene.

Conventional designs can utilize higher pressures in the deethanizer in an effort to limit/reduce isobutane losses from the process in the deethanizer overhead. However, as noted above, a downside of this higher pressure in the deethanizer is the requirement of the dehexanizer overhead compressor and increased steam consumption in the deethanizer to accomplish the desired separation, especially when substantial amounts (e.g., 50%) of olefin-free isobutane (OFIC4) are desired, as discussed further hereinbelow.

Disclosed herein are various aspects of systems, apparatuses, and methods related to polymerization reactions, for example, polyethylene polymerization. The systems, apparatuses, and methods are generally related to a process for the separation and handling of the effluent stream from a polymer (e.g., polyethylene) production process.

Figure 1A:
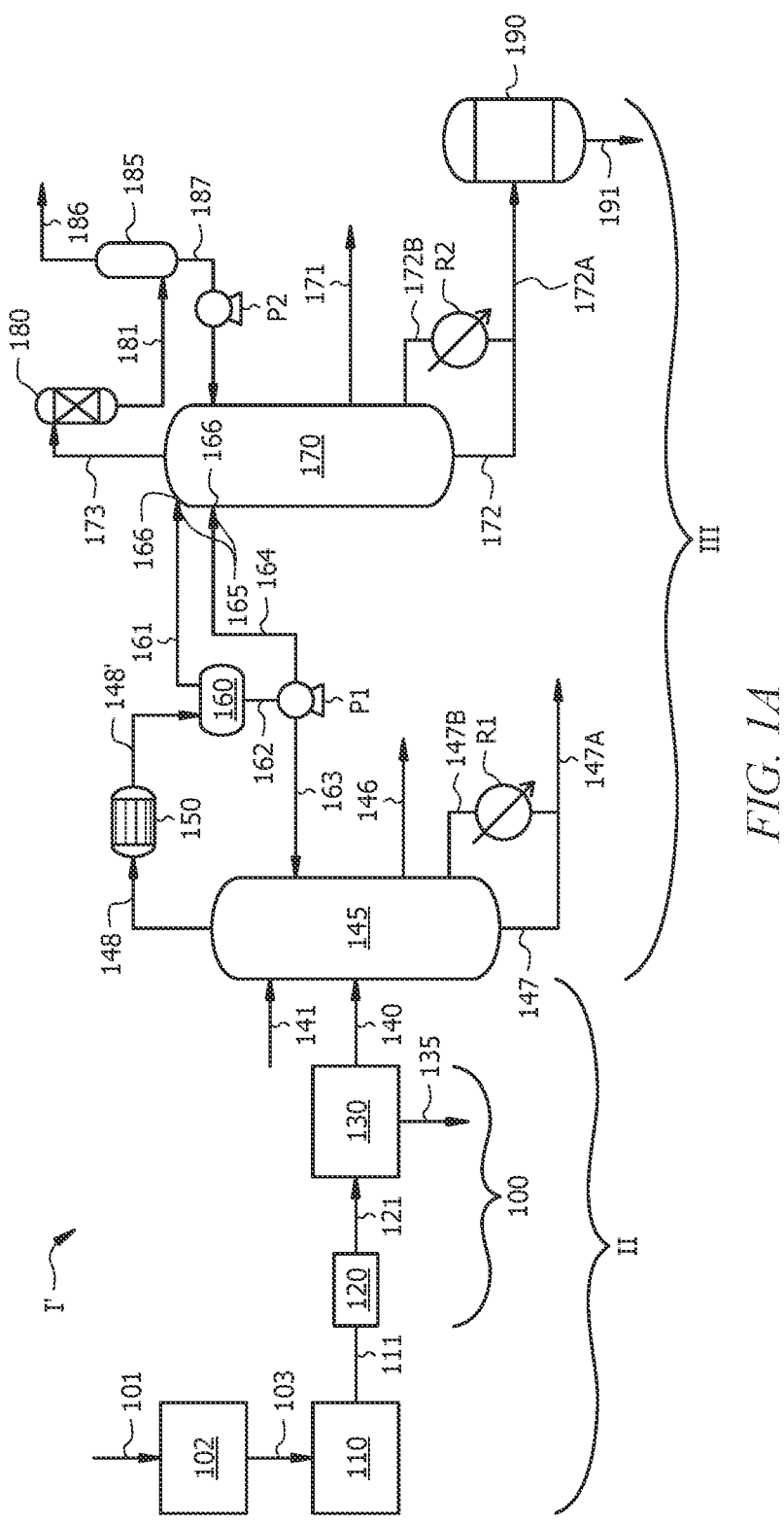
FIG. 1A is a schematic of a polymerization system or polymer production system (PPS), according to aspects of this disclosure.
Figure 1B:
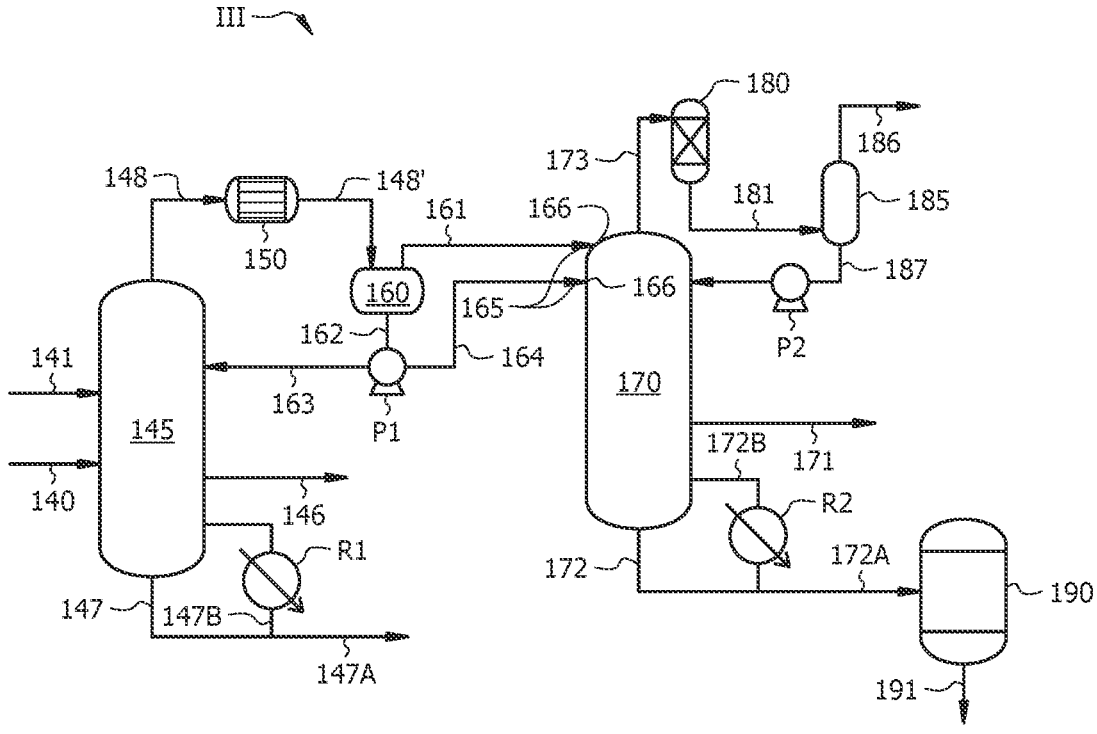
FIG. 1B is a schematic of a flash gas treatment system (FGTS), according to aspects of this disclosure.
Figure 1C:
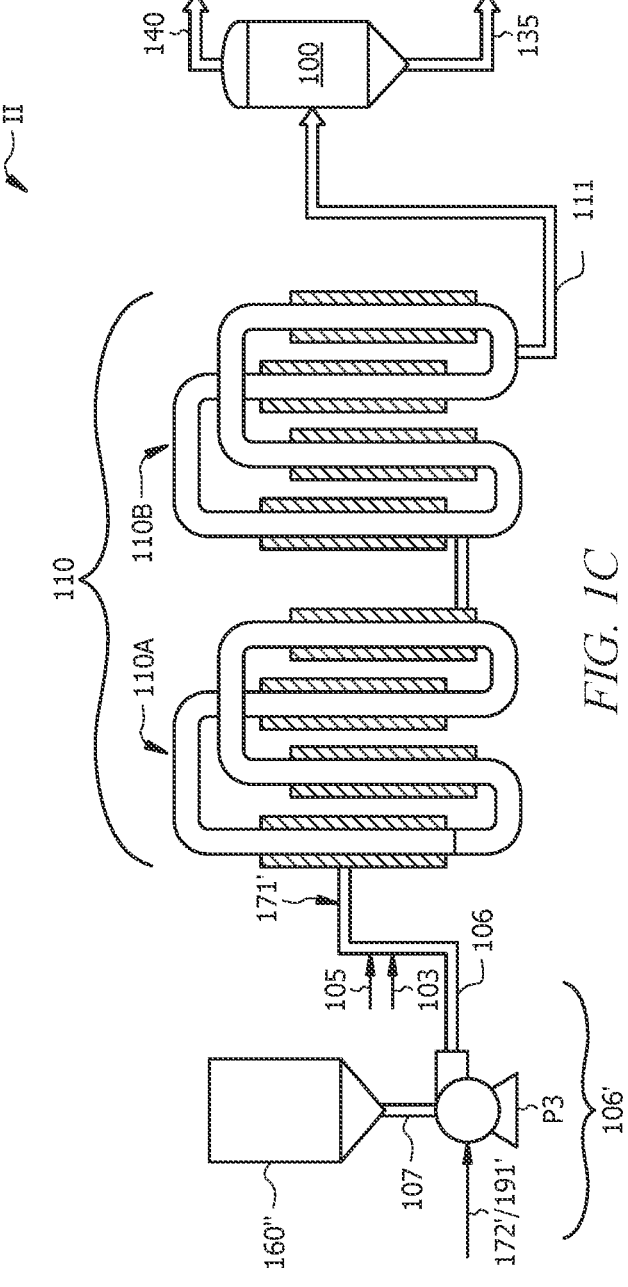
FIG. 1C is a schematic of a flash gas production system (FGPS) operable to produce a flash gas, according to aspects of this disclosure.
Figure 1D:
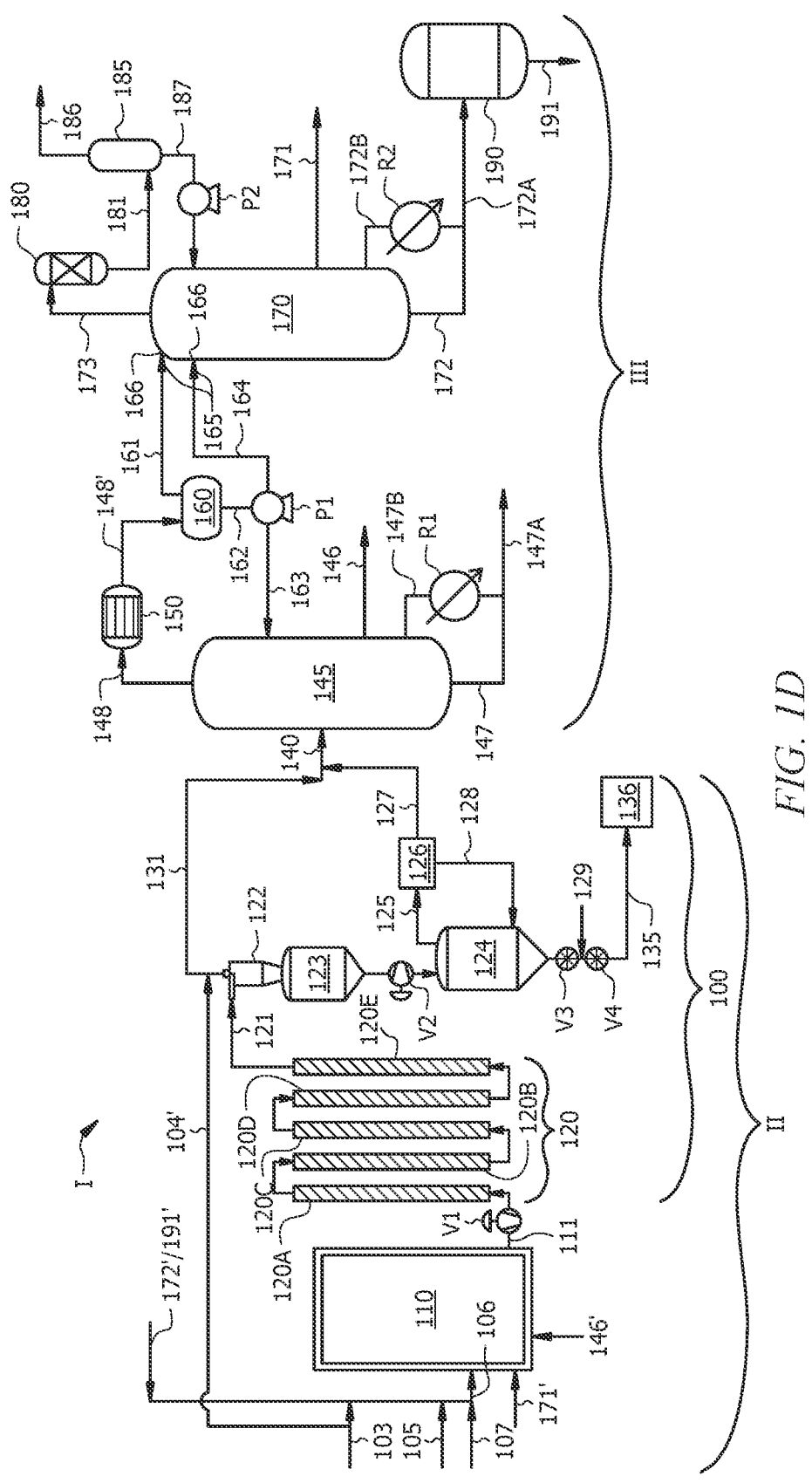
FIG. 1D is a schematic of a polymerization system, according to aspects of this disclosure.
Figure 2:
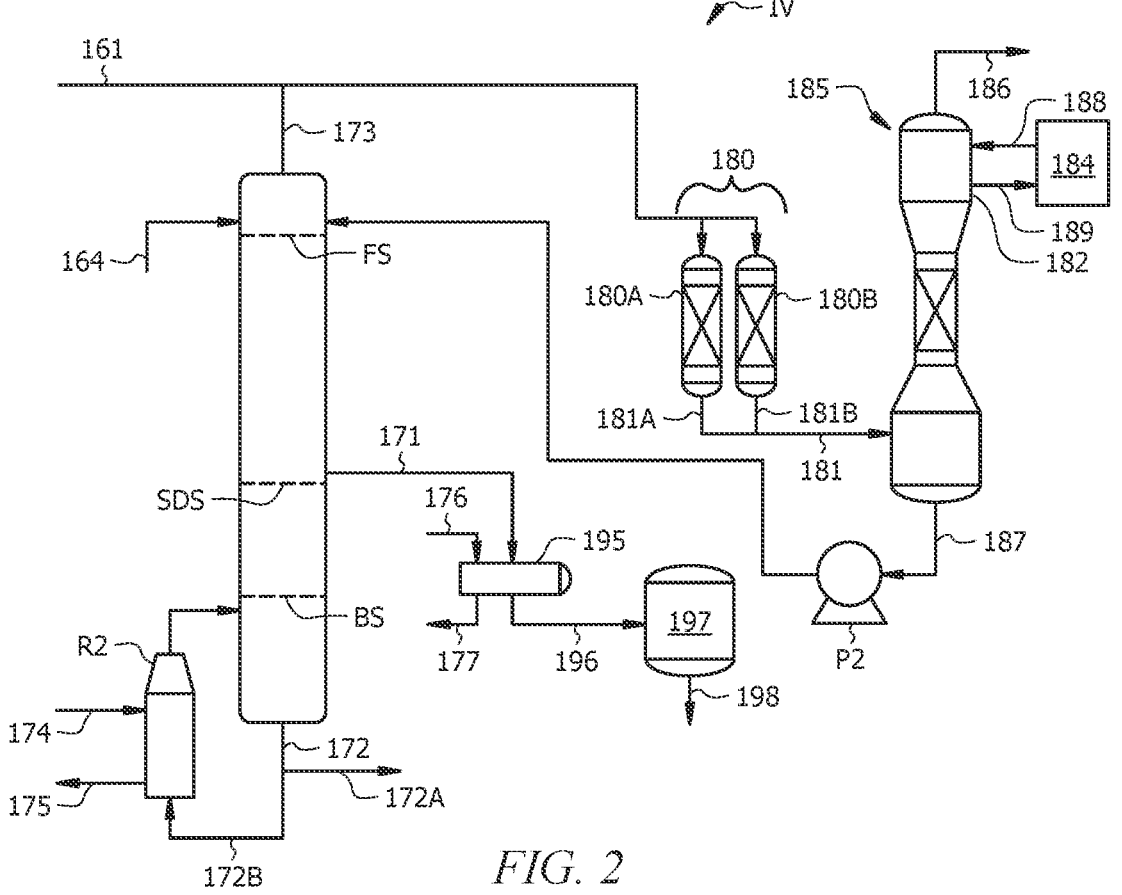
FIG. 2 is a schematic of a portion of a flash gas treatment system (FGTS), according to aspects of this disclosure.

FIG. 1A is a schematic of a polymerization system I comprising a flash gas production system (FGPS) II and a flash gas treatment system (FGTS) III, according to aspects of this disclosure; FIG. 1B is a schematic of a flash gas treatment system (FGTS) III, according to aspects of this disclosure; FIG. 1C is a schematic of a FGPS II operable to produce a flash gas, according to aspects of this disclosure; and FIG. 1D is a schematic of a polymerization system I', according to aspects of this disclosure;

Referring to FIG. 1A, a polymer (e.g., polyethylene) production system (PPS) I is disclosed. PPS system I generally comprises a flash gas production system (FGPS) II and a flash gas treatment system (FGTS) III. PPS I can comprise a purifier 102, polymerization reactor or reactor system 110, one or more (e.g., flash-line) heaters 120, a flash chamber 130, a first column 145, a gas/liquid separator (e.g., an accumulator) 160, a second column 170, a vent column 185, or a combination thereof. In aspects disclosed herein, various such system components can be in fluid communication via one or more conduits (e.g., pipes, tubing, flow lines, etc.) suitable for the conveyance of a particular stream, for example as shown in FIGS. 1A-2 by the streams which are conveyed via such conduits. In alternative aspects, the same or similar equipment and/or processes can be employed for the production of a variety of polymeric materials, for example, polyethylene, polypropylene, polybutylene, polyvinylchloride, or the like.

With reference to FIG. 1A, PPS I comprises: a FGPS II comprising one or more polymerization reactor(s)/system 110 (also referred to as a polymerization reactors 110 or polymerization system 110) configured to produce a polymerization reactor effluent stream 111; and flash apparatus 100 (also referred to herein as a flash system 100) configured for flashing the polymerization reactor(s)/system effluent stream 111 (also referred to simply as a "polymerization reactor effluent stream 111") to form a flash gas stream 140; and a FGTS III comprising a first column 145 configured to separate the flash gas stream 140 into a first column overhead stream 148, a first column side stream 146 (also referred to as a "hexene recycle stream 146" or simply "side stream 146"), and a first column bottoms stream 147; a liquid/vapor separator 160 configured for separating the first column overhead stream 148 into a gas/vapor stream 161 and a liquid stream 162; and a second column 170 configured to receive a feed 165 (via one or more feed inlets 166) comprising the gas stream 161 and at least a portion 164 of the liquid stream 162 and separate the feed 165 to produce a second column overhead stream 173, a second column side stream 171 (also referred to herein as a recycle isobutane or RIC4 stream 171, and a second column bottoms stream 172 (also referred to herein as an olefin-free isobutane or OFIC4 stream 172.

FGPS II can include a polymerization feed purifier 102 (also referred to simply as a "feed purifier 102" or a "feed stream purifier 102") operable to purify a polymerization feed stream 101 (also referred to simply as a "feed stream 101"), thus providing a purified feed 103 (also referred to herein as a "feed stream 103" or a "polymerization feed stream 103") for introduction into polymerization system 110. In aspects, the purifier 102 can comprise a device or apparatus suitable for the purification of one or more reactant gases in a feed stream which can comprise a plurality of potentially unwanted gaseous compounds, elements, contaminants, or the like. Non-limiting examples of a suitable feed purifier 102 can comprise a filter, a membrane, a reactor, an absorbent, a molecular sieve, one or more distillation columns, fractionation columns, or combinations thereof. The purifier 102 can be configured to separate ethylene from a feed stream 101 comprising ethylene and further comprising methane, ethane, acetylene, propane, propylene, water, oxygen, other gaseous hydrocarbons, various contaminants, and/or combinations thereof. The purified polymerization feed 103 can comprise substantially pure monomers (e.g., ethylene monomers), as will be described herein. A portion 104' of feed stream 103 can be combined with flash gas 131, in embodiments.

Flash apparatus 100 of FGPS II can comprise one or more heaters 120 and a flash chamber 130. One or more heaters 120 can be utilized to heat the polymerization system effluent stream 111. The heated effluent stream 121 from the one or more heaters 120 can be introduced into flash chamber 130. Within flash chamber 130, flash gas 140 can be separated from polymer product 135 (also referred to herein as "polymer fluff 135" or simply "polymer 135"). The polymer product 135 can comprise, for example, polyethylene (PE), polypropylene (PP), polybutylene (PB), polyvinylchloride (PVC), or the like.

The FGTS III can generally comprise a three-column fractionation train to meet the demands of (1) rejecting heavy and light impurities, (2) recycling 1-hexene (e.g., via first column side stream 146, described hereinbelow), and (3) providing recycle isobutane (in second column side stream 171, which is also referred to herein as RIC4 171) and substantially olefin free isobutane (in second column bottoms stream 172, which is also referred to herein as OFIC4 172). The three columns in the fractionation train of FGTS III can comprise: (1) first column 145 (e.g., a dehexanizer column), configured for taking upstream fluids (e.g., primarily flash gas 140) to reject heavies (e.g., in first column bottoms stream 147), recycle 1-hexene (e.g., via first column side stream 146) and provide feed 165 to second (e.g., deethanizer) column 170; (2) second column 170 (e.g., a deethanizer column), configured to provide RIC4 171 and OFIC4 172, provide feed (e.g., second column overhead stream 173) to the third column (e.g., vent column) 185; and (3) the third column (e.g., vent column) 185, to recover components (e.g., isobutane, ethylene) from the vent column feed (e.g., second column overhead stream 173) from deethanizer second column 170 and reject lights 186.

PPS I (and FGTS III) comprises no compressor between the first column 145 and the second column 170. Second column 170 can be configured for operation at a pressure within about 10% of a pressure at which the first column 145 is operated. First column 145, second column 170, or both can comprise a fractionation/distillation column. In aspects, polymer product 135 comprises polyethylene (PE), and first column 145 comprises a dehexanizer column configured to separate hexane and heavier components from the flash gas stream 140 to provide the first column overhead stream 148.

The first column overhead stream 148 can comprise less than or equal to about 10, 5, 4, 3, 2, 1 or 0.5 ppmv C6+ (e.g., compounds containing 6 or more carbon atoms). In aspects, first column overhead stream 148 comprises from about 85 to about 100, from about 80 to about 90, or from about 85 to about 90 vol. % isobutane, from about 0 to about 2, from greater than 0 to about 3, or from 0.001 to about 2 vol % hydrogen, from about 2 to about 15, from about 0 to about 15, from greater than 0 to 15, or from greater than 0 to 10 vol % ethylene. For example, in aspects, first column overhead stream 148 can comprise, from about 3 to about 4 ppm vol. C6+, from about 85.6 to about 87.2 vol % isobutane, from about 0.04 to about 1.3 vol % H2, and/or from about 6.1 to about 10.1 vol % ethylene.

The first column side stream 146 can comprise from about 85, 90, or 95 to about 95, 98, or 99 vol. % hexene. In aspects, the first column side stream 146 can comprise from about 80 to 100 vol % hexene and from about 0 to about 20 vol % C6+. For example, in aspects, first column side stream 146 can comprise from about 94.6 to about 96.2 wt % 1-hexene, from about 2.6 to about 4.2 wt % N-hexane, and/or less than about 1 wt % isobutane. All or a portion of first column side stream 146 can be recycled. For example, all or a portion of first column side stream 146 can be recycled to first column 145 (e.g., via an inlet line 141), all or a portion of first column side stream 146 can be recycled to polymerization reactor/system 110 (e.g., to first polymerization reactor 110A of an advanced dual loop reactor, such as described hereinbelow with reference to FIG. 1C), or a combination thereof. Accordingly, PPS I can include recycle line or path fluidly connecting first column side stream 146 with (e.g., inlet line 141 of) first column 145, (e.g., a polymerization reactor 110A, 110B of (discussed hereinbelow with reference to FIG. 2)) polymerization system 110, or both. One or more inlet lines 141 can be configured to introduce one or more additional components to first column 145. For example, an inlet line 141 can be configured/utilized to introduce fresh or recycle hexene to first column 145, an inlet line 141 can be configured/utilized to introduce fresh or recycle isobutane to first column 145, or a combination thereof. As discussed hereinbelow, in aspects, recycled isobutane in second column side stream 171 is recycled to first column 145 via one or more inlet lines 141.

The first column bottoms stream 147 can comprise primarily C6+ (e.g., compounds containing six or more carbon atoms; such as hexane, oils, oligomers, or a combination thereof). For example, in aspects, first column bottoms stream 147 can comprise from about 0 to about 50 vol % hexane, from about 0 to about 25 vol % oligomers, from about 0 to about 25 vol % oils, from about 0 to about 90 vol % hexene, or a combination thereof. In aspects, first column bottoms stream 147 can comprise from about 5 to about 12 wt % hexane, from about 1 to about 30 wt % oligomers, or a combination thereof. A portion 147B of first column bottoms stream 147 can be returned to first column 145 via first column reboiler R1, and a portion 147A of first column bottoms stream 147 not returned to first column 145.

With reference to FIG. 1B, which is a schematic of the FGTS III, according to aspects of this disclosure, FGTS III comprises first column 145, gas/liquid separator 160, and second column 170. FGTS III can further include a condenser 150 upstream of gas/liquid separator 160. The condenser 150 can be configured to cool the first column overhead stream 148 to provide cooled first column overhead stream 148', to further condense components therein for separation in gas/liquid separator 160. The liquid/vapor separator 160 can comprise an overhead accumulator (also referred to simply as "an accumulator 160" or "gas/liquid separator 160") configured to separate the cooled first column overhead stream 148' into a gas stream 161 (also referred to herein as a "gas/vapor stream 161") and a liquid 162 (also referred to herein as a "liquid stream 162"). Liquid 162 from accumulator 160 can be divided into portion of liquid stream 164 that can be pumped (e.g., via pump P1) to second column 170 as a component of second column feed 165 (also referred to herein simply as "feed stream 165"), and liquid reflux stream 163 returned to first column 145.

In aspects, polymer product 135 comprises polyethylene (PE), and second column 170 comprises a deethanizer column configured to separate ethane and lighter components in second column overhead stream 173 from the feed 165 to produce second column side stream 171 and second column bottoms stream 172. The second column bottoms stream 172 can comprise less than or equal to about 5, 4, 3, 2, or 1 ppmw C2−, (e.g., compounds having two or fewer carbon atoms). In aspects, a second column bottoms stream 172 outlet line can be configured for a second column bottoms stream 172 flow rate of isobutane and a second column side stream 171 outlet line is configured for a second column side stream 171 flow rate of isobutane, a total flow rate of isobutane comprises the bottoms stream 172 flow rate and the side stream 171 flow rate, and the bottoms stream 172 flow rate comprises less than or equal to about 15, 20, or 25 volume percent (vol. %) of the total flow rate and the side stream 171 flow rate comprises greater than or equal to about 85, 80, or 75 vol. % of the total flow rate.

In aspects, second column bottoms stream 172 can comprise from about 95 to about 96 wt % isobutane, from about 5 to about 10 ppmw (e.g., about 8 ppmw) olefins (such as 1 ppm ethylene, 7 ppm 1-hexene), and essentially no hydrogen. Second column bottoms stream 172 can comprise up to 5 ppmw ethylene and/or 500 ppmw hexene, in aspects. In aspects, the second column side stream 171 can comprise from about 50, 60, 70, 80, or 90 to about 80, 90, or 95 vol. % isobutane (e.g., from 90 to 95 vol % isobutane), from about 0, 5, or 8 to about 5, 6, 7, 8, 9, or 10 vol % olefins (e.g., from 2 to 5 vol % ethylene), and from about 1, 2, 3, 4, or 5 to about 10, 9, 8, 7, or 6 vol % hydrogen (e.g., less than about 1 ppb hydrogen). For example, in aspects second column side stream 171 can comprise from about 91-93 wt % isobutane, from about 2 to about 4 wt % ethylene, and less than about 1 ppb hydrogen. In aspects, second column overhead stream 173 can comprise from about 45, 50, or 55 to about 55, 50, or 45 vol %, or less than or equal to about 55, 50, or 45 vol % isobutane, from about 20, 25, or 30 to about 35, 40, or 45 vol %, or less than or equal to about 45, 40, or 35 vol % ethylene, and/or from about 0, 5, or 10 to about 20, 15, or 10 vol %, or less than or equal to about 15, 14, 13, 12, 11, or 10 vol % hydrogen, from about 0.1, 0.5, or 1 to about 5, 4, 3, 2, or 1 vol %, or less than or equal to about 5, 4, 3, 2, or 1 vol % ethane. For example, in aspects, second column overhead stream 173 can comprise from about 0.5 to about 14.5 vol % hydrogen, from about 23 to about 45 vol % ethylene, from about 0.5 to about 4.5 vol % ethane, and/or from about 52 to about 56 vol % isobutane. In aspects, second column overhead stream 173 can comprise from about 50 to about 90 vol % isobutane, from about 0 to 10 to vol % ethylene, up to 10 vol % hydrogen and up to 15 vol % ethane.

As noted above, FGTS III/PPS I can include a recycle path for recycling at least a portion 171' (also referred to herein as "recycle isobutane 171" or "recycle RIC4") of the second column side stream 171. For example, such a recycle path can be configured to introduce the at least the portion of the second column side stream 171 to at least one of the one or more polymerization reactors/polymerization system 110 as a recycle isobutane stream. As noted hereinabove, the recycle isobutane stream (RIC4, e.g., second column side stream 171) can comprise greater than or equal to about 90 volume percent (vol %) (e.g., from about 90 to about 93 wt %) isobutane, greater than or equal to about 5 ppmw olefins (e.g., 2 to 4 wt % ethylene, 4-5 ppmw 1-hexene), less than or equal to about 0.1 vol % hydrogen (e.g., less than 1 ppbw hydrogen), less than about 5 wt % n-butane (e.g., about 3 wt % n-butane), less than about 0.5 wt % C3 (e.g., 0.1 to about 0.2 wt % C3s), less than about 1 wt % ethane (e.g., 0.1 to 0.7 wt % ethane), or a combination thereof. The olefins can comprise ethylene, hexene, or a combination thereof.

In aspects, second column bottoms stream 172 is a substantially olefin-free isobutane stream (OFIC4) comprising greater than or equal to about 90 volume percent (vol %), or from about 90, 91, 92, 93, or 94 to about 93, 94, 95, 96 vol % isobutane (e.g., from about 95 to about 96 wt % isobutane), less than or equal to about 5, 4, 3, 2, or 1 ppmw olefins (e.g., less than or equal to about 1 ppmw ethylene, less than or equal to about 7 ppmw hexene), less than or equal to about 5, 4, 3, 2, or 1 ppmw other paraffins (e.g., less than or equal to about 5 wt % n-butane, less than 3 ppmw ethane), substantially no (e.g., less than about 0.1 ppmw) hydrogen, less than 0.1 wt % C3s (e.g., 0.03 to 0.06 wt %

C3s), or a combination thereof, wherein the olefins comprise ethylene, hexene, or a combination thereof.

With reference to FIG. 1C, which is a schematic of a flash gas production system (FGPS) II operable to produce a flash gas 140, according to aspects of this disclosure, and which will be described in further detail hereinbelow, PPS I can further comprise a catalyst pretreater 106' upstream of the one or more polymerization reactor(s)/system 110. PPS I can further include a recycle path for recycling at least a portion 172' of the substantially olefins-free isobutane stream (e.g., second column bottoms stream 172) from the second column 170 as a recycle olefins-free isobutane stream 172' to the catalyst pretreater 106'. The catalyst pretreater 106' can be configured to produce (and provide via a pump P3) a catalyst slurry 106 comprising a polymerization catalyst 107 and the recycle olefins-free isobutane stream 172'/191'. Polymerization catalyst 107 from catalyst hopper 160" can be combined olefin-free diluent (e.g., with recycle olefin-free isobutane 172' from second column bottoms stream 172 and/or recycle substantially olefin-free isobutane 191' from an olefin-free isobutane storage tank 190). Portion 172' is also referred to herein as "recycle olefin-free isobutane 172'")

As noted hereinabove, second column 170 can be in operation at a second column pressure and the first column 145 can be in operation at a first column pressure; the second column pressure can be within about 10% of the first column pressure. In aspects, the second column pressure is from about 110 psig to about 160 psig. For example, the second column 170 pressure can be about 110, 120, 130, 140, 150, or 160 psig, in aspects.

As best seen in FIG. 2, which is a schematic of a portion IV of a flash gas treatment system (FGTS), according to aspects of this disclosure, FGTS III can further include a second column reboiler R2 associated with the second column 170. A portion of second column bottoms stream 172 can be returned to second column 170 via second column reboiler R2. Heating fluid (e.g., steam) 174 can be introduced to second column reboiler R2, and spent (e.g., cooled) heating fluid removed from second column reboiler R2 via condensate line 175. A reboiler duty of the second column reboiler R2 associated with the second column 170 can be less than a reboiler duty of a reboiler associated with a second column in a same system designed to effect a same separation of isobutane in second column side stream 171 and second column bottoms stream 172 except wherein the second column is not operated at a second column pressure that is within about 10% of the first column pressure. A diameter of the second column 170 can be less than a diameter of the second column utilized to provide the same separation in the same system operated at the second column pressure that is not within about 10% of the first column pressure.

As depicted in FIGS. 1A-1D, and noted above, PPS I and FGTS III do not comprise any compressor for compressing of the first column overhead stream 148, the gas stream 161, or the at least the portion 164 of the liquid stream 162 prior to introduction of the gas stream 161 and the at least the portion 164 of the liquid stream 162 as feed 165 to the second column 170. In aspects, PPS I and FGTS III also comprise no preheater for preheating of the feed 165 or components thereof (e.g., the gas stream 161, the liquid stream 162, the portion 164 of the liquid stream 162) between the second column 170 and the first column 145.

With reference back to FIG. 2, which provides the schematic of the portion IV of flash gas treatment system III comprising second column 170 and vent column 185, a liquid side draw stage SDS is a stage from which or tray from immediately above which the second column side stream 171 is withdrawn, and a feed stage FS is a stage to which or a tray immediately above which the second column feed 165 is introduced to the second column 170. The stages can be numbered from the top. The bottom stage BS is located closer to a bottom of the second column 170 than the feed stage FS. According to aspects of this disclosure, the liquid side draw stage SDS of the second column 170 can be separated from the feed stage FS of the second column 170 by more than 5, 6, 7, 8, 9, 10, 11, 12, 13, 14, or 15 theoretical or actual stages (trays), or by from about 3 to about 20, from about 5 to about 18, or from about 10 to about 15 theoretical or actual stages (trays).

In aspects. PPS I and/or FGTS III is configured to produce the second column side stream 171 comprising less than or equal to about 0.1 vol % hydrogen, greater than or equal to about 0.5 vol % ethylene, greater than or equal to about 90 vol % isobutane, or a combination thereof. In aspects, a desired composition of the second column side stream 171 and/or the second column bottom stream 172 can be obtained by utilizing a PPS I.

PPS I and/or FGTS III can be configured for maximizing an amount of ethylene in the second column side stream 171 (e.g., for recycle, for example, to polymerization system 110), while maintaining a concentration of hydrogen in the second column side stream 171 below a tolerance of the one or more polymerization reactor(s)/system 110 (e.g., at less than about 0.1, 0.5 or 1% ppmw volume percent (vol %) $H_2$), and comprising a recycle path for recycling at least a portion 171' of the second column side stream 171 to at least one of the one or more polymerization reactor(s)/system 110.

With reference to FIG. 1C, the one or more polymerization reactors/polymerization system 110 can comprise an advanced dual loop (ADL) polymerization reactor(s)/system 110 comprising a first polymerization reactor 110A upstream of a second polymerization reactor 110B and optionally downstream of a catalyst pretreater 106'. Catalyst slurry 106 and feed stream 103 (e.g., olefin, such as ethylene), and additional reactants 105 (e.g., hydrogen) can be introduced into ADL polymerization reaction system 110. First polymerization reactor 110A can be configured to produce a higher molecular weight polymer of a bimodal polymer, and second polymerization reactor 110B can be configured to produce a lower molecular weight polymer of the bimodal polymer. The higher molecular weight polymer has a higher average molecular weight than the lower molecular weight polymer. At least a portion 171' of the second column side stream 171 can be recycled to the first polymerization reactor 110A, the second polymerization reactor 110B, or both.

The polymerization reactor effluent stream 111 from the ADL reactor 110 can be introduced (e.g., via valve V1) into flash apparatus 100 to produce the polymer product 135 and the flash gas 140 to be treated in downstream FGTS III. In aspects, second polymerization reactor 110B tolerates a higher hydrogen concentration than first polymerization reactor 110A. In aspects, the system and method of this disclosure provide for a second column side stream 171 that comprises a level of hydrogen low enough for introduction into first polymerization reactor 110A, second polymerization reactor 110B, or both, with approximately 85% or more of the total diluent (e.g., isobutane) flow (further comprising unreacted ethylene and a low level of hydrogen) exiting second column 170 with second column side stream 171 and less than or equal to about 15 volume percent of the diluent exiting second column 170 as recycle OFIC4 via second column bottoms stream 172.

The one or more polymerization reactors 110 (e.g., first polymerization reactor 110A, second polymerization reactor 110B) contain a polymerization catalyst 107, which is further described hereinbelow.

The FGTS III/PPS I can further include one or more overhead treaters 180, with a first overhead treater 180A and a second overhead treater 180B depicted in the aspect of FIG. 2. The one or more overhead treaters 180 can be configured to remove one or more components from second column overhead stream 173 prior to introduction of treated second column overhead stream 181 (e.g., comprising first overhead treater outlet stream 181A and second overhead treater outlet stream 181B) into vent column 185. The overhead treaters 180 can be configured to remove moisture (e.g., water) and prevent hydrates from forming in the vent condenser. The two treaters can be operated in parallel, with one online while the other is standing by and/or being regenerated. Vent column 185 can include a condenser/condensing section 182 for condensing the treated second column overhead stream 181, and can separate the treated second column overhead stream 181 into a vent column overhead gas 186 and a vent column bottom liquid 187. A reflux pump P2 can be operable to return at least a portion of the vent column bottom liquid 187 to the second column 170 as reflux, and a vent or outlet for venting at least a portion of the vent column overhead gas 186 (e.g., to a cracker). Refrigerant (e.g., propane) 188 can be introduced into condenser/condensing section 182 of vent column 185, and spent refrigerant 189 removed therefrom.

With continued reference to FIG. 2, second column side stream 171 can be cooled in recycle isobutane cooler 195. Cooled second column side stream 196 can be stored in a recycle diluent tank 197. Relatively cold coolant can be introduced into recycle isobutane cooler 195 via line 176 and relatively warm coolant removed therefrom via line 177. Recycle diluent (e.g., a portion of cooled second column side stream 196) can be recycled, for example, to the one or more polymerization reactor(s)/system 110 via second column bottom stream 172, cooled second column side stream 196, and/or recycle diluent tank outlet line 198.

In aspects, the second column 170 is operating/operated at a second column operating pressure, and the first column 145 is operating/operated at a first column operating pressure, the second column operating pressure is within about 10% of the first column operating pressure, and an amount of ethylene in the vent column overhead gas 186 being vented is less than or equal to an amount of ethylene vented in a same system configured for a same separation of isobutane between the second column side stream 171 and the second column bottoms stream 172 except without having the second column pressure within about 10% of the first column pressure.

With reference to FIG. 1D, which is a schematic of a PPS I', according to aspects of this disclosure, FGPS II can include polymerization system or reactor(s) 110 configured for the production of polymerization effluent stream 111 comprising polymer (e.g., PE), unreacted reactants, diluent, etc. Olefin-free diluent (e.g., olefin-free isobutane) 172'/191' from second column bottoms stream 172 and/or olefin-free diluent storage tank 190/olefin-free storage tank outlet line 191, respectively, can be combined with polymerization catalyst and/or co-catalyst 107 to form catalyst slurry 106 for introduction into the polymerization reactor(s)/system 110. Olefin (e.g., hexene, ethylene) can be introduced into polymerization reactor(s)/system 110 via, for example, one or more feedstream(s) 103. Diluent (e.g., recycle isobutane 171') can also be introduced into polymerization reactor(s)/system 110.

Flash apparatus 100 can include one or more flash line heaters (FLHs) 120, with five (120A, 120B, 120C, 120D, 120E) depicted in the aspect of FIG. 1D. Heated effluent stream 121 can be introduced into flash gas cyclone 122 of flash apparatus 100. Gas 131 separated from the polymer product in flash gas cyclone can be removed from flash gas cyclone 122. Polymer from flash gas cyclone 122 can be introduced into surge tank 123. From surge tank 123, solids including polymer product can be metered (e.g., via valve V2) to a purge column 124. Purge column 124 can be configured to remove additional gas from the polymer fluff. Gas 125 extracted from the polymer fluff in purge column 124 can be introduced into an isobutane nitrogen recovery unit (INRU) 126, configured to separate nitrogen 128 for recycle to purge column 124 from INRU liquid 127. The INRU liquid 127 can be combined with the flash gas 131 to provide flash gas 140 for introduction to FGTS III. Polymer product 135 from purge column 124 can be sent for further processing, for example to an extruder 136. Transport gas 129 (e.g., nitrogen) and one or more metering valves (e.g., rotary valve V3, rotary valve V4) can be utilized to flow polymer fluff 135 from purge column 124 to extruder 136. Other FGPS II can be utilized to produce the flash gas 140 for introduction into FGTS III; the FGPS II and flash apparatus 100 of FIGS. 1A, 1C, and 1D are provided by way of examples.

In aspects, a polymerization system of this disclosure comprises: one or more polymerization reactors 110 configured to produce a polymerization reactor effluent stream 111; flash apparatus 100 (e.g., a flash chamber 130) configured for flashing the polymerization reactor effluent stream 111 to form a flash gas stream 140; a first column 145 configured to separate the flash gas stream 140 into a first column overhead stream 148, a first column side stream 146, and a first column bottoms stream 147; a liquid/vapor separator 160 configured for separating the first column overhead stream 148 into a gas stream 161 and a liquid stream 162; and a second column 170 configured to receive a feed 165 comprising the gas stream 161 and at least a portion 164 of the liquid stream 162 and separate the feed 165 to produce a second column overhead stream 173, a second column side stream 171, and a second column bottoms stream 172, wherein the second column 170 is operating at a second column pressure, and wherein the first column 145 is operating at a first column pressure, wherein the second column pressure is within about 10% of the first column pressure.

In aspects, a polymerization system of this disclosure comprises: one or more polymerization reactors 110 configured to produce a polymerization reactor effluent stream 111; flash apparatus 100 (e.g., a flash chamber 130) configured for flashing the polymerization reactor effluent stream 111 to form a flash gas stream 140; a first column 145 configured to separate the flash gas stream 140 into a first column overhead stream 148, a first column side stream 146, and a first column bottoms stream 147; a liquid/vapor separator 160 configured for separating the first column overhead stream 148 into a gas stream 161 and a liquid stream 162; a second column 170 configured to receive a feed 165 comprising the gas stream 161 and at least a portion 164 of the liquid stream 162 and separate the feed 165 to produce a second column overhead stream 173, a second column side stream 171, and a second column bottoms stream 172, and a recycle path (e.g., a recycle line(s)) for recycling at least a portion 171' of the second column side stream 171 to at least one of the one or more polymerization reactors 110. The system I can be configured such that an amount of ethylene in the second column side stream 171 is maximized, while a concentration of hydrogen in the second column side stream 171 is below a tolerance of the one or more polymerization reactors 110 (e.g., at less than about 0.1, 0.5, or 1% ppmw $H_2$).

In aspects, the PPS I/FGTS III of this disclosure comprises no dehexanizer overhead compressor or associated suction drum and pump, no deethanizer column feed economizer, no deethanizer feed preheater, no deethanizer overhead condenser, no deethanizer accumulator, or a reduced number of deethanizer reflux pumps, or a combination thereof.

Various aspects of suitable PPS systems having been disclosed, aspects of a flash gas treatment process will now be disclosed. One or more of the aspects of a flash gas treatment process can be described with reference to PPS I. Although a given flash gas treatment process may be described with reference to one or more aspects of a PPS, such a disclosure should not be construed as limiting. Although the various steps of the processes disclosed herein may be disclosed or illustrated in a particular order, such should not be construed as limiting the performance of these processes to any particular order unless otherwise indicated.

Also disclosed herein are methods of treating a polymerization reactor effluent stream 111 and/or a flash gas 140. The method can include producing polymerization reactor effluent stream 111 via a PPS, such as PPS I/I' as described hereinabove with reference to FIGS. 1A and 1D; producing the flash gas 140 via a FGPS, such as FGPS II described hereinabove with reference to FIGS. 1A-1D, and treating the flash gas 140 via a FGTS, such as FGTS III described hereinabove with reference to FIG. 1A, FIG. 1B, and FIG. 1D. A method of this disclosure can comprise: recovering a polymerization reactor effluent stream 111 from one or more polymerization reactors 110; flashing the polymerization reactor effluent stream 111 (e.g., in flash system or apparatus 100) to form a flash gas stream 140; separating, in a first column 145, the flash gas stream 140 into a first column overhead stream 148, a first column side stream 146, and a first column bottoms stream 147; separating the first column overhead stream 148 into a gas stream 161 and a liquid stream 162; and introducing a feed 165 comprising the gas stream 161 and at least a portion 164 of the liquid stream 162 to a second column 170 to produce a second column overhead stream 173, a second column side stream 171, and a second column bottoms stream 172. The second column bottoms stream 172 can have a second column bottoms stream 172 flow rate of diluent (e.g., isobutane) and the second column side stream 171 can have a second column side stream 171 flow rate of diluent (e.g., isobutane). A total flow rate of diluent (e.g., isobutane) from second column 170 can comprise the second column bottoms stream 172 flow rate and the second column side stream 171 flow rate. The second column bottoms stream 172 flow rate can comprise less than or equal to about 15 volume percent (vol. %) of the total flow rate of diluent and the second column side stream 171 flow rate can comprise greater than or equal to about 85 vol. % of the total flow rate of diluent.

The method can further comprise purifying a polymerization feed stream 101 to provide a purified polymerization feed stream 103 and polymerizing monomers of the purified feed stream 103 in one or more polymerization reactors 110 to provide the polymerization reactor effluent stream 111. In aspects, a polymerization feed stream 101 is purified. Purifying the feed stream 101 can comprise separating unwanted compounds and elements from a feed stream comprising ethylene to form a purified polymerization feed stream 103. In aspects illustrated by FIG. 1A, purifying the feed stream 101 can comprise routing the feed stream 101 to a feed stream purifier 102, such as described hereinabove.

In aspects, purifying a feed stream 101 can yield a purified feed stream 103 comprising substantially pure ethylene. In aspects, the purified feed stream 103 can comprise less than 25% by weight, alternatively, less than about 10%, alternatively, less than about 1.0% of any one or more of nitrogen, oxygen, methane, ethane, propane, other hydrocarbons, or combinations thereof. As used herein "substantially pure ethylene" refers to a fluid stream comprising at least about 60% ethylene, alternatively, at least about 70% ethylene, alternatively, at least about 80% ethylene, alternatively, at least about 90% ethylene, alternatively, at least about 95% ethylene, alternatively, at least about 99% ethylene by weight, alternatively, at least about 99.5% ethylene by weight. In aspects, the purified feed stream 103 can further comprise trace amounts of ethane.

The method can further include polymerizing monomers of the purified stream 103 in the polymerization reactor(s)/ system 110 to yield a polymerization system effluent stream 111 generally comprising unreacted monomers (e.g., ethylene), ethane, diluent (e.g., one or more of propane, propylene, isobutane, n-butane, etc.), and a polymerization product (e.g., polyethylene).

In aspects, monomers of the purified feed stream 103 are polymerized. Polymerizing monomers of the purified feed stream 103 can comprise allowing a polymerization reaction between a plurality of monomers by contacting a monomer or monomers with a catalyst system under conditions suitable for the formation of a polymer. A suitable catalyst system/polymerization catalyst 107 can comprise a catalyst and, optionally, a co-catalyst and/or promoter. Non-limiting examples of suitable catalyst systems include Ziegler-Natta catalysts, Ziegler catalysts, chromium catalysts, chromium oxide catalysts, chromocene catalysts, metallocene catalysts, nickel catalysts, or combinations thereof. Catalyst systems suitable for use in this disclosure have been described, for example, in U.S. Pat. No. 7,619,047 and U.S. Patent Application Publication Nos. 2007/0197374, 2009/0004417, 2010/0029872, 2006/0094590, and 2010/0041842, each of which is incorporated by reference herein in its entirety. In aspects, any suitable catalyst system can be employed, as may be appropriate for a given process or product need or desire.

In the aspect illustrated in FIG. 1A, polymerizing monomers of the purified feed 103 can comprise routing the purified feed stream 103 to the polymerization reactor(s)/ polymerization system 110. In aspects disclosed herein, the polymerization reactor(s)/system 110 can comprise any vessel or combination of vessels suitably configured to provide an environment for a chemical reaction (e.g., a contact zone) between monomers (e.g., ethylene) and/or polymers (e.g., an active or growing polymer chain) in the presence of a polymerization catalyst 107 to yield a polymer 135 (e.g., a polyethylene polymer). Although the aspects of FIG. 1A and FIG. 1D illustrate a PPS I/I' having one polymerization reactor, one of skill in the art viewing this disclosure will recognize that two or more reactors arranged in any suitable configuration (e.g., in series and/or in parallel) can be employed. For example, FGPS II of FIG. 1B, described hereinabove, depicts an advanced dual loop polymerization reactor system 110 comprising two polymerization reactors, including first polymerization reactor 110A and second polymerization reactor 110B.

As used herein, the terms "polymerization reactor" or "reactor" include any polymerization reactor (e.g., a vessel) capable of polymerizing olefin monomers to produce homopolymers or copolymers. Such homopolymers and copolymers may be referred to as resins or polymers. The various types of reactors include those that may be referred to as batch, slurry, gas-phase, solution, high pressure, tubular, or autoclave reactors. Gas phase reactors may comprise fluidized bed reactors or staged horizontal reactors. Slurry reactors may comprise vertical or horizontal loops. High pressure reactors may comprise autoclave or tubular reactors. Reactor types can include batch and/or continuous processes. Continuous processes may use intermittent or continuous product discharge. Processes may also include partial or full direct recycle of un-reacted monomer, un-reacted comonomer, and/or diluent.

Polymerization reactor systems of the present disclosure can comprise one type of reactor in a system. Alternatively, in aspects where multiple reactors are employed, two or more reactors of the same or different type can be employed. Production of polymers in multiple reactors may include several stages in at least two separate polymerization reactors interconnected by a transfer device or conduit making it possible to transfer the polymers resulting from the first polymerization reactor into the second reactor. The desired polymerization conditions in one of the reactors may be different from the operating conditions of the other reactors. Alternatively, polymerization in multiple reactors may include the transfer of polymer from a first reactor to a subsequent reactor(s) for continued polymerization. Multiple reactor systems may include any combination including, but not limited to, multiple loop reactors, multiple gas reactors, a combination of loop and gas reactors, multiple high pressure reactors or a combination of high pressure with loop and/or gas reactors. The multiple reactors may be operated in series or in parallel, or any combination thereof.

According to aspects of this disclosure, the polymerization reactor may comprise at least one gas phase reactor. In an alternative aspect, the polymerization reactor may comprise at least one gas phase reactor in combination with at least one other reactor, which may be a slurry loop reactor or a solution polymerization reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 5,352,749, 4,588,790 and 5,436,304, each of which is incorporated by reference in its entirety herein.

According to another aspect of the disclosure, the polymerization reactor system may additionally comprise at least one loop slurry reactor comprising vertical or horizontal loops. Monomer, diluent, catalyst, and optionally any comonomer may be continuously fed to a loop reactor where polymerization may occur. Generally, continuous processes may comprise the continuous introduction of a monomer, a catalyst, and a diluent into a polymerization reactor and the continuous removal from this reactor of a suspension comprising polymer particles and the diluent. Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, iso-pentane, neopentane, and n-hexane. Some loop polymerization reactions can occur under bulk conditions where no diluent is used. An example of polymerization of propylene monomer is disclosed in U.S. Pat. No. 5,455,314, which is incorporated by reference herein in its entirety. A typical slurry polymerization process (also known as the particle form process), is disclosed, for example, in U.S. Pat. Nos. 3,248,179, 4,501,885, 5,565,175, 5,575,979, 6,239,235, 6,262,191 and 6,833,415, each of which is incorporated by reference in its entirety herein. In aspects, any suitable type, form, style, or combination of polymerization reactor or reactors may be employed in a given application.

According to yet another aspect of the disclosure, the polymerization reactor may comprise a solution polymerization reactor wherein the monomer is contacted with the catalyst composition by suitable stirring or other means. A carrier comprising an inert organic diluent or excess monomer may be employed. If desired, the monomer may be brought in the vapor phase into contact with the catalytic reaction product, in the presence or absence of liquid material. The polymerization zone may be maintained at temperatures and pressures that result in the formation of a solution of the polymer in a reaction medium. Agitation may be employed to obtain better temperature control and to maintain uniform polymerization mixtures throughout the polymerization zone. Adequate means may be utilized for dissipating the heat of polymerization.

Polymerization reactors suitable for the present disclosure may further comprise any combination of at least one raw material feed system, at least one feed system for catalyst or catalyst components, at least one recycle system, and/or at least one polymer recovery system. Suitable reactor systems for the present disclosure may further comprise systems for feedstock purification, catalyst storage and preparation, extrusion, reactor cooling, polymer recovery, fractionation, recycle, storage, load-out, laboratory analysis, process control, and/or other systems.

Conditions that may be controlled for polymerization efficiency and to provide desired resin properties include time, temperature, pressure and the concentrations of various reactants. Polymerization temperature can affect catalyst productivity, polymer molecular weight and molecular weight distribution. Suitable polymerization temperature may be any temperature below the de-polymerization temperature according to the Gibbs Free energy equation. Typically this includes from about 60° C. to about 280° C., for example, and from about 70° C. to about 110° C., depending upon the type of polymerization reaction.

Suitable contact time of the components of the polymerization process may vary, as may be appropriate for a given process or product need or desire. In addition to contact time for the polymerization reaction itself, any/all times for pre-contacting, pre-activation, activation, aging, conditioning, or other process relating to the polymerization step may be varied, as may be necessary or desired to achieve an appropriate outcome.

Suitable pressures will also vary according to the reactor and polymerization type. The pressure for liquid phase polymerizations in a loop reactor is typically less than 1000 psig. Pressure for gas phase polymerization is usually at about 200 to 500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages. In aspects, polymerization may occur in an environment having a suitable combination of temperature and pressure. For example, polymerization may occur at a pressure in a range from about 425 psi to about 900 psi, alternatively, about 450 psi to about 675 psi, and a temperature in a range from about 60° C. to about 280° C., alternatively, from about 70° C. to about 110° C.

The concentration of various reactants can be controlled to produce resins with certain physical and mechanical properties. The proposed end-use product that will be formed by the resin and the method of forming that product determines the desired resin properties. Mechanical properties include tensile, flexural, impact, creep, stress relaxation and hardness tests. Physical properties include density, molecular weight, molecular weight distribution, melting temperature, glass transition temperature, temperature melt of crystallization, density, stereoregularity, crack growth, long chain branching and rheological measurements.

The concentrations and/or partial pressures of monomer, co-monomer, hydrogen, co-catalyst, modifiers, and electron donors are important in producing these resin properties. Comonomer may be used to control product density. Hydrogen may be used to control product molecular weight. Co-catalysts can be used to alkylate, scavenge poisons and control molecular weight. Modifiers can be used to control product properties and electron donors affect stereoregularity, the molecular weight distribution, or molecular weight. In addition, the concentration of poisons is minimized because poisons impact the reactions and product properties.

In aspects, polymerizing monomers of the purified feed may comprise introducing a suitable catalyst system 107 into the reactor(s) 110, so as to form a catalyst slurry 106. Alternatively, a suitable catalyst system may reside in the polymerization reactor(s)/system 110.

As explained above, polymerizing monomers of the purified feed 103 may comprise selectively manipulating one or more polymerization reaction conditions to yield a given polymer product 135, to yield a polymer product 135 having one or more desirable properties, to achieve a desired efficiency, to achieve a desired yield, the like, or combinations thereof. Non-limiting examples of such parameters include time, temperature, pressure, type and/or quantity of catalyst or co-catalyst, the concentrations and/or partial pressures of various reactants, or other process parameters. In aspects, polymerizing monomers of the purified feed 103 may comprise adjusting one or more polymerization reaction conditions.

In aspects, polymerizing monomers of the purified feed 103 may comprise maintaining a suitable temperature, pressure, and/or partial pressure(s) during the polymerization reaction, alternatively, cycling between a series of suitable temperatures, pressures, and/or partials pressure(s) during the polymerization reaction.

In aspects, polymerizing monomers of the purified feed 103 may comprise circulating, flowing, cycling, mixing, agitating, or combinations thereof, the monomers, catalyst system, and/or the slurry within the polymerization reactor(s)/system 110. In aspects where the monomers, catalyst system, and/or slurry are circulated, circulation may be at a velocity (e.g., fluid velocity) of from about 1 m/s to about 30 m/s, alternatively, from about 2 m/s to about 17 m/s, alternatively, from about 3 m/s to about 15 m/s.

In aspects, polymerizing monomers of the purified feed 103 may comprise configuring the polymerization reactor(s)/system 110 to yield a multimodal (e.g., a bimodal) polymer (e.g., polyethylene). For example, the resultant polymer 135 may comprise both a relatively high molecular weight, low density (HMWLD) polyethylene polymer and a relatively low molecular weight, high density (LMWHD) polyethylene polymer. For example, various types of suitable polymers may be characterized as having different densities. For example, a Type I may be characterized as having a density in a range of from about 0.910 g/cm³ to about 0.925 g/cm³, alternatively, a Type II may be characterized as having a density from about 0.926 g/cm³ to about 0.940 g/cm³, alternatively, a Type III may be characterized as having a density from about 0.941 g/cm³ to about 0.959 g/cm³, alternatively, a Type IV may be characterized as having a density of greater than about 0.960 g/cm³.

Polymerizing monomers of the purified feed 103 in polymerization reactor(s)/system 110 may yield an effluent stream 111, which may generally comprise various solids, semi-solids, volatile and nonvolatile liquids, gases and/or combinations thereof. For example, the polymerization reactor effluent stream 111 may comprise unreacted reactant monomers (e.g., unreacted ethylene monomers) liquids, diluents, waste products, other gases, and/or contaminants. In aspects, the effluent stream 111 may comprise hydrogen, nitrogen, methane, ethylene, ethane, propylene, propane, butane, isobutane, pentane, hexane, hexene-1 and heavier hydrocarbons and polymer product (e.g., polyethylene). In aspects, ethylene may be present in a range of from about 0.1% to about 15%, alternatively, from about 1.0% to about 10%, by weight. Ethane may be present in a range of from about 0.001% to about 4%, alternatively, from about 0.2% to about 2% by weight. Isobutane may be present in a range from about 70% to about 99%, alternatively, from about 80% to about 98%, alternatively, about 83% to about 97% by weight. The solids and/or liquids may comprise a polymer product (e.g., a polyethylene polymer), often referred to at this stage of the process as "polymer fluff", or simply "fluff."

The method can include heating the polymerization reactor effluent stream 111 in heater 120 to yield a heated effluent stream 121. The method can further include separating the heated effluent stream 121 in flash chamber 130 to provide a polymer product stream 135 and a flash gas stream 140. In aspects, heat may be added to effluent stream 111. For example, energy (e.g. heat) may be added to effluent stream 111 to facilitate processing (separation of the components of effluent stream 111, as will be discussed herein). In aspects, heating the effluent stream 111 can be accomplished by any suitable device, apparatus, or process as will yield component states and/or phases, increases in effluent stream temperature, or combinations thereof as may be desired for a given application. In shown in the aspects of FIG. 1A and FIG. 1D, heating the effluent stream 111 can comprise routing the effluent stream 111 through a suitable heater 120, for example, flash-line heater. As used herein, the term "flash-line heater" may refer to a device or apparatus configured and arranged to add heat to a stream (e.g., effluent stream 111, which may comprise solids, liquids, and/or gases). Suitable flash-line heaters as may be employed herein are disclosed in U.S. Pat. Nos. 3,152,872; 5,183,866; and 5,207,929, each of which is incorporated herein in its entirety. An example of a suitable flash-line heater is a heat exchanger. Such a heat exchanger may comprise a double-walled pipe in which the substance to be heated (e.g., effluent stream 111) flows through an inner pipe while steam is injected in an outer or surrounding pipe. In aspects, the flash-line heater may operate intermittently. Generally, the volume of material flowing through a heat exchanger and the speed at which it flows determine the amount of heat that will be added. In aspects, heating the effluent stream 111 may yield a heated effluent stream 121.

In alternative aspects, heat is not be added to effluent stream 111. For example, in aspects, the polymerization reaction may occur at temperatures, pressures, and/or other operating parameters as may provide sufficient energy to make unnecessary the addition of heat or energy to the effluent stream 111.

In aspects, the heated effluent stream 121 (alternatively, in aspects where the effluent stream has not been heated, the effluent stream 111) may be separated into a polymer product stream 135 and a flash gas stream 140. In aspects, separating the heated effluent stream 121 into a polymer product stream 135 and a flash gas stream 140 can be by any suitable device, apparatus, or process. For example, in aspects, separating an effluent stream (such as heated effluent stream 121 or effluent stream 111) into a polymer product stream 135 and a flash gas stream 140 can comprise flashing the effluent stream. Not intending to be bound by theory, "flashing" a stream generally refers to causing a phase change in which liquid phase components of a stream (e.g., the heated effluent stream 121) are converted into gas phase components (e.g. vaporizing/gasifying the liquid components of the stream), for example, as by a reduction of the pressure of the stream. In aspects, flashing may be accomplished by adding heat to a stream, reducing the pressure of the stream, adding other forms of energy to the stream (e.g. ultrasonic energy), or combinations thereof. For example, flashing a stream may comprise rapidly (e.g., instantaneously or nearly instantaneously) allowing the volume of the stream to increase such that the pressure of the stream falls and the liquid components of the stream enter a vapor or gas phase. As such, a stream that has been flashed can comprise gaseous phase components (e.g., the flash gas) and solid phase components (e.g., the polymer product). For example, in aspects, substantially all (e.g., at least 98%, alternatively 99%, alternatively 99.5%, alternatively 99.9%) by total weight of the heated effluent stream 121 of non-polymer components (e.g., liquids and gases) present in stream 121 are recovered as gases via flash gas stream 140.

In aspects, separating polymerization effluent stream 111 (e.g., the heated effluent stream 121) into a polymer product stream 135 and a flash gas stream 140 can generally comprise segregating the gas phase components from the solid phase components. Segregating the gas phase components and the solid phase components may be by any suitable device, apparatus, or process. For example, as depicted in the aspect of FIG. 1D, in aspects where a stream has been flashed, the solid phase components (e.g., the polymer product 135) and the vapor phase components (e.g., the flash gas 140) can be separated by cyclonic separation. Generally speaking, cyclonic or vortex separation refers to a method of separating solid, and/or particulate materials from gaseous materials, for example, via a high speed rotating flow established within a cylindrical or conical container (e.g., a cyclonic chamber or cyclone, such as flash gas cyclone 122). Material flows in a spiral pattern, beginning at the top (wide end) of the cyclone and ending at the bottom (narrow) end before exiting the cyclone. Not intending to be bound by theory, solid and/or particulate material (e.g. the polymer fluff) entrained within a rotating, gaseous stream within the cyclone have too much inertia to follow the tight curve of the rotating, gaseous stream and, thus, strike the outside wall of the cyclone, and fall toward the bottom of the cyclone. In such a conical system, as the rotation flow moves towards the narrow end of the cyclone the rotational radius of the stream is reduced, separating smaller and smaller particles. The cyclone geometry, together with flow rate, defines the "cut point" of the cyclone; that is, the size of particle that will be removed from the stream with 50% efficiency. Generally, particles having a size larger than the cut point will be removed with a greater efficiency, and smaller particles with a lower efficiency.

In an alternative aspect, the solid phase components may be sufficiently segregated from the gaseous components upon flashing (e.g., vaporization) of the stream and without the need to subject the solid phase components and the gaseous components to any further segregating process. For example, the solid materials that had been entrained within the stream may "fall out" when the liquid components of the stream undergo a phase change to vapor.

In the aspect of FIG. 1A, separating the heated effluent stream 111 comprises routing the heated effluent stream 121 into the flash chamber 130. Flash chamber 130 may comprise a single vessel or multiple vessels, as suitable, and may comprise additional flash compartments or chambers, cyclonic separators, flush/surge chambers, various valves, inlets, outlets, filters (such as bag filters), or other suitable equipment. Not seeking to be bound by theory, as the heated effluent stream 121 is introduced into the flash chamber 130, the volume of the stream entering the flash chamber 130 may expand rapidly, resulting in a decrease in the pressure of the stream and the vaporization of the liquid components of the heated effluent stream 121. As such, in aspects, introduction of the heated effluent stream 121 into the flash chamber 130 (e.g., flashing the heated effluent stream 121) may yield solid components (e.g., polymer product or polymer fluff) and gaseous or vaporous components (e.g., flash gases). Also in the aspect of FIG. 1D, the polymer product 135 may be segregated from the flash gases 140 by cyclonic separation as described above.

In the aspect of FIG. 1A, the solid components of the heated effluent stream 121 can exit the flash chamber 130 as a polymer product stream 135 and the gaseous or vaporous components as flash gas stream 140. In aspects, the polymer product stream 135 may comprise polymer fluff comprising oligomers and/or larger polymers, as produced in the polymerization reaction or reactions described previously (e.g., polyethylene). In aspects, the flash gas stream 140 may comprise the non-solid components of the effluent stream 111 in the vapor phase (e.g., hydrogen, nitrogen, methane, ethylene, ethane, propylene, propane, butane, isobutane, pentane, hexane, hexene-1 and heavier hydrocarbons).

In aspects, the flash gas stream 140 can exit the flash chamber 130 at a suitable pressure. For example, the pressure of flash gas stream 140 as it exits flash chamber 130 may be within a pressure range of from about 14.7 psia to about 527.9 psia, alternatively, from about 15.7 psia to about 348 psia, alternatively, from about 85 psia to about 290 psia.

In aspects, separating the heated effluent stream 121 (alternatively, in aspects where the effluent stream has not been heated, the effluent stream 111) into a polymer product stream 135 and a gaseous stream (e.g. flash gas stream 140) may be by filtration, membrane separation, various forms of centrifugal separation, or other suitable device, apparatus, or process of separation as will be appreciated by one of ordinary skill in the art with the aid of this disclosure.

The method can further comprise returning at least a portion 146' of the first column side stream 146 (e.g., comprising hexene) to at least one of the one or more polymerization reactors 110. The first column 145, the second column 170, or both can comprise a fractionation/distillation column.

In aspects, as noted above, the first column 145 comprises a dehexanizer column configured to separate hexane and heavier components from the flash gas stream 140 to provide the first column overhead stream 148. The first column 145 can be operated to produce the first column overhead stream 148 comprising less than or equal to about 5 ppmw C6+. In aspects, the first column 145 can be operated to produce first column overhead stream 148 comprising greater than or equal to about 90 vol % isobutane, from about 0 to about 3 vol % hydrogen, from about 0 to about 15 vol % ethylene, or a combination thereof. For example, in aspects, first column overhead stream 148 comprises from about 3 to about 4 ppm vol. C6+, from about 85 to about 90 vol. % isobutane, from about 0.04 to about 1.5 vol % hydrogen, from about 5 to about 10 vol % ethylene, or a combination thereof.

In aspects, first column 145 can be operated to produce the first column side stream 146 comprising from about 0 to about 5 vol % hexene. For example, in aspects, first column side stream 146 comprises from about 94 to about 96 wt % 1-hexene, from about 2.5 to about 4.5 wt % n-hexane, and less than about 1 wt % isobutane.

In aspects, the first column 145 can be operated to produce first column bottoms stream 147 comprising primarily C6+ (e.g., hexane, oils, oligomers, or a combination thereof). One or more additional components (e.g., hexene, such as recycled from first column side stream 146, and/or isobutane (e.g., recycled from second column side stream 171)) can be introduced into first column 145 via one or more inlets 141.

A portion 147B of first column bottoms stream 147 can be returned to first column 145 via first column reboiler R1. A portion (e.g., liquid reflux stream 163) of liquid 162 can be returned as reflux to first column 145 via pump P1.

The method can thus include separating the flash gas stream 140 into a first column overhead stream 148, a first column side stream 146, and a first column bottoms stream 147. In aspects, separating the flash gas stream 140 may generally comprise segregating parts of the flash gas stream 140 on the basis of various differences in physical or chemical properties between those parts. In aspects, separating the flash gas stream 140 into a first column overhead stream 148, a first column side stream 146, and a first column bottoms stream 147 can generally comprise separating the flash gas stream 140 into a first column overhead stream 148 comprising $C_4$ and lighter hydrocarbons and any other gases (e.g., hydrogen or nitrogen), a first column bottom stream 147 comprising $C_6$ and heavier compounds such as alkanes, and a first column side stream 146 comprising hexene.

In aspects, separating the flash gas stream 140 into first column overhead stream 148, first column side stream 146, and a first column bottom stream 147 can occur by any suitable device, apparatus, or process. Nonlimiting examples of such a suitable process include fractionation, distillation, and the like. Not intending to be bound by theory, fractionation refers to a separation process in which a mixture is separated into a number of parts based on differences in a given property of those parts. In aspects, it may be possible to separate components of a mixture in a single run via fractionation. Not intending to be bound by theory, distillation refers to a separation process in which a mixture is separated based on differences in the volatilities of the components of the mixture. Generally speaking, distillation involves adding heat to a mixture, allowing the various components of the mixture to volatilize into the vapor phase, and then collecting the individual components as they condense at different points within the distillation column.

In the aspect of FIG. 1A, separating the flash gas stream 140 into first column overhead stream 148, first column side stream 146, and first column bottom stream 147 comprises routing the flash gas stream 140 to the first column 145. In aspects, the first column 145 can comprise a fractionation tower (or fractionation column). In an alternative aspect, the first column 145 can comprise a distillation column (or distillation tower). In aspects, first column 145, can be provided with one or more inlets and at least three outlets. The first column 145 can be operated at suitable temperature and pressure, for example as may be suitable to achieve separation of the components of the flash gas stream 140. For example, the first column 145 can be operated at a temperature in a range of from about 15° C. to about 233° C., alternatively, from about 20° C. to about 200° C., alternatively, from about 20° C. to about 180° C., and/or a pressure in a range of from about 14.7 psi to about 527.9 psi, alternatively, from about 15.7 psi to about 348 psi, alternatively, from about 85 psi to about 290 psi. The first column 145 may be configured and/or sized provide for separation of a suitable volume of gases (e.g., the flash gas stream 140). As will be appreciated by one of skill in the art viewing this disclosure, the flash gas stream 140 may remain and/or reside within first column 145 for any suitable amount of time, for example an amount of time as may be necessary to provide sufficient separation of the components of flash gas stream 140.

In aspects, the flash gas stream 140 can be introduced into the first column 145 without a compressive step, that is, without compression of the flash gas stream after it is emitted from the flash apparatus 100/flash chamber 130 and before it is introduced into the first column 145. In another aspect, the flash gas stream 140 may be introduced into the first column 145 at substantially the same pressure as the outlet pressure of flash chamber 130 (e.g., a pressure of from about 14.7 psia to about 527.9 psia, alternatively, from about 15.7 psia to about 348 psia, alternatively, from about 85 psia to about 290 psia at the outlet of the flash chamber 130). In another aspect, the flash gas stream 140 may be introduced into the first column 145 without a significant compressive step. In aspects, flash gas stream 140 may be introduced into first column at a pressure in a range of from about 25 psi less than the pressure at which the flash gas stream was emitted from the flash chamber to about 25 psi greater than the pressure at which the flash gas stream was emitted from the flash chamber, alternatively, from about 15 psi less than the pressure at which the flash gas stream was emitted from the flash chamber to about 15 psi greater than the pressure at which the flash gas stream was emitted from the flash chamber, alternatively, from about 5 psi less than the pressure at which the flash gas stream was emitted from the flash chamber to about 5 psi greater than the pressure at which the flash gas stream was emitted from the flash chamber. In aspects, the flash gas stream 140 may be introduced into the first column 145 at a pressure in a range of from about 14.7 psia to about 527.8 psia, alternatively, from about 15.7 psia to about 348 psia, from about 85 psia to about 290 psia.

In aspects, the first column 145 can be configured and/or operated such that each of the first column overhead stream 148, the first column bottom stream 147, and the first column side stream 146 can comprise a desired portion, part, or subset of components of the flash gas stream 140. For example, as will be appreciated by one of skill in the art with the aid of this disclosure, the location of a particular stream outlet, the operating parameters of the first column 145, the composition of the flash gas stream 140, or combinations thereof may be manipulated such that a given stream may comprise a particular one or more components of the flash gas stream 140.

In aspects, first column overhead stream 148 can be characterized as comprising $C_4$ and lighter hydrocarbons (e.g., butane, isobutane, propane, ethane, or methane) and any light gases e.g., hydrogen or nitrogen). For example, $C_4$ and lighter hydrocarbons and gases may be present in the first column overhead stream 148 in an amount of from about 80% to about 100% by total weight of the first column overhead stream 148, alternatively from about 90% to about 99.999999%, alternatively from about 99% to about 99.9999%, alternatively, $C_5$ and heavier hydrocarbons may be present in the first column overhead stream 148 in an amount from 0% to about 20% by total weight of the first column overhead stream 148, alternatively from about 10% to about 0.000001%, alternatively from about 1.0% to about 0.0001%. Also, for example, at least 90% by weight of the flash gas stream 140 of the $C_4$ and lighter hydrocarbons and gases may be present in the first column overhead stream 148, alternatively, at least 98%, alternatively, at least 99%.

In aspects, the first column bottom stream 147 can be characterized as comprising $C_6$ and heavier components such as alkanes, that is, alkanes larger than hexane (e.g., heptane and/or other large alkanes). In aspects, hydrocarbons other than $C_6$ and heavier alkanes may be present in the first column bottom stream 147 in an amount less than about 15%, alternatively, less than about 10%, alternatively, less than about 5% by total weight of the first bottom stream 147. In aspects, the first column bottom stream 147 can be directed to additional processing steps or methods, or alternatively they may be disposed of, as appropriate. In aspects, first column bottom stream 147 can be directed to a flare for disposal.

In aspects, first column side stream 146 can be characterized as comprising hexene. For example, hexene may be present in first column side stream 146 in an amount of from about 20% to about 98% by total weight of the first column side stream 146, alternatively from about 40% hexene to about 95%, alternatively from about 50% hexene to about 95% hexene.

In aspects, at least a portion of the first column bottom stream 147 can be returned to the first column 145. For example, in the example of FIG. 1A, a portion of the first column bottom stream 147 is routed, via a first column reboiler R1, to the first column 145 for additional processing.

In aspects, at least a portion 146' of the first column side stream 146 can be recycled. In the aspect of FIG. 1A, recycling the first column side stream 146 can comprise routing, for example, via a suitable pump or compressor, the first column side stream 146 back to and/or introducing the side stream 146 into the PPS I, for example, for reuse in a polymerization reaction. Recycling the first column side stream 146 (e.g., comprising hexene) may provide an efficient and/or cost-effective means of supplying hexene for operation of the polymerization reaction process. In aspects, the hexene of side stream 146 can be employed in the polymerization reaction as, for example, a comonomer in the reaction. In alternative or additional aspects, first column side stream 146 can be routed to storage for subsequent use in a polymerization reaction or employed in any other suitable process.

In aspects, the method comprises separating the flash gas stream 140 in first column 145 to provide a first column overhead stream 148 generally comprising $C_4$ and smaller/lighter hydrocarbons, a first column bottom stream 147 generally comprising $C_6$ and larger/heavier hydrocarbons, and a first column side stream 146 generally comprising hexene. The method can further comprise separating the first column overhead stream 148 in a gas/liquid separator (e.g., an accumulator) 160 to yield a gas stream 161 generally comprising light gases (e.g., hydrogen, nitrogen), isobutane, ethylene, ethane, and/or other light hydrocarbons, and a liquid stream 162 generally comprising isobutane, ethylene, ethane, and/or other hydrocarbons. The method can further include separating the gas stream 161 in second column 170 to yield a second column overhead stream 173 comprising substantially ethylene, a second column side stream generally comprising isobutane and ethylene and a low level of hydrogen and a second column bottoms stream 172 generally comprising olefin-free isobutane.

In aspects, the first column overhead stream 148 can thus be separated into a gas stream 161 and a liquid stream 162. Separating the first column overhead stream 148 into the gas stream 161 and the liquid stream 162 can generally comprise separating the first column overhead stream 148 into a gas stream 161 comprising butane and lighter hydrocarbons and any other gases (e.g., hydrogen or nitrogen) and a liquid stream 162 comprising isobutane.

In aspects, the first column overhead stream 148 can be separated by any suitable device apparatus, or process. Nonlimiting examples of suitable means of separation include accumulation, settling, condensation, membrane separation, flashing, distillation, fractionation, or the like. Not intending to be bound by theory, accumulation refers to a separation process in which components of a mixture are separated on the basis of weight and/or density. For example, the mixture may be introduced into a vessel (an accumulating vessel or accumulator) in which the lighter (less dense) components are allowed to rise toward the top of the vessel while the heavier (more dense) are allowed to fall toward the bottom of the vessel. In aspects, the first column overhead stream 148 can comprise gaseous or vaporous components, liquid components (e.g., such components having cooled and/or condensed, for example, via flow through a condenser 150) or combinations thereof. In such aspects, the liquid components may be separated from the gaseous components in an accumulator.

As noted above, the method can comprise separating the first column overhead stream 148 into a gas stream 161 and a liquid stream 162. Separating the first column overhead stream 148 into a gas stream 161 and a liquid stream 162 can be effected by condensing the first column overhead stream 148 in a condenser 150 to produce a cooled first column overhead stream 148', introducing the cooled first column overhead stream 148' into an accumulator 160, and extracting a gas stream 161 and a liquid 162 from the accumulator 160.

With reference to the aspect of FIG. 1A, separating the first column overhead stream 148 into a gas stream 161 and a liquid stream 162 can comprise routing the first column overhead stream 148 into accumulator 160. As illustrated in the aspect of FIG. 1A, the first column overhead stream 148 can be routed to the accumulator 160 via a condenser 150, for example to remove heat from the stream and/or allow at least a portion of the stream to condense into a liquid phase. In aspects, the accumulator 160 can generally comprise any suitable vessel as will allow for the separation of the components of the first column overhead stream 148 (e.g., as disclosed above). The accumulator 160 can comprise one or more compartments or chambers, valves, at least one inlet, and two or more outlets. In aspects, the accumulator 160 can permit the lighter components of first column overhead stream 148 to rise to the top of accumulator 160 and the heavier components to fall to the bottom of the accumulator 160. For example, in aspects where the first column overhead stream 148 comprises both liquid and gaseous phases, the vapor phase components may rise toward the top and the liquid phase components may fall to the bottom of the accumulator 160. In aspects, the lighter components (e.g., the vapor phase components) may be emitted from the accumulator as the gas stream 161 and the heavier components (e.g., the liquid phase components) may be emitted as the liquid stream 162. The accumulator 160 may be operated at a suitable temperature and pressure, for example, as may be suitable to cause condensation of at least one component of the first column overhead stream 148. For example, the accumulator 160 may be operated at a temperature in a range of from about 10° C. to about 100° C., alternatively, from about 15° C. to about 60° C., alternatively, from about 20° C. to about 50° C., and a pressure in a range of from about 14.7 psia to about 527.9 psia, alternatively, from about 15.7 psia to about 348 psia, alternatively, from about 85 psia to about 290 psia.

In aspects, the accumulator 160 can be configured and/or operated such that each of the gas stream 161 and the liquid stream 162 comprise a desired portion, part, or subset of components of the first column overhead stream 148. For example, as will be appreciated by one of skill in the art with the aid of this disclosure, the operating parameters of the accumulator 160, the composition of the first column overhead stream 148, or combinations thereof may be manipulated such that a given stream may comprise a particular one or more components of the first column overhead stream 148.

In aspects, gas stream 161 can be characterized as comprising butane, lighter hydrocarbons, and non-condensable gases (e.g., butane, isobutane, propane, ethane, methane, oxygen, helium hydrogen, nitrogen, or carbon dioxide). For example, butane and lighter hydrocarbons may be present in the gas stream 161 in an amount from about 90% to about 100 by total weight of the gas stream 161, alternatively, from about 95% to about 99.9999%, alternatively, from about 98% to about 99%. Also, for example, species heavier than butane may be present in the gas stream 161 in an amount less than about 1%, alternatively, less than about 0.01%, alternatively, less than about 0.0001%. The flow rate of gas stream 161 may be such that sufficient propane, lighter hydrocarbons, and non-condensable gases (e.g., propylene, ethane, methane, oxygen, helium hydrogen, nitrogen, or carbon dioxide) are removed overhead in vent column overhead gas stream 186 to prevent build up in the system.

In aspects the liquid stream 162 can be characterized as comprising isobutane. For example, isobutane may be present in the liquid stream 162 in an amount from about 70% to about 100% by total weight of the liquid stream 162, alternatively, from about 75% to about 99%, alternatively, from about 80% to about 98%. Also, for example, ethylene may be present in the liquid stream 162 in an amount from about 0% to about 10 or 20% by total weight of the liquid stream 162, alternatively, from about 0.5 or 1% to about 10 or 15%, alternatively, from about 2% to about 10 or from about 3 to about 6%.

In aspects, for example, as illustrated in FIG. 1A, at least a portion 163 of liquid stream 162 may be introduced into first column 145 as a reflux stream. In the aspect of FIG. 1A, the reflux stream may be taken from the accumulator 160 and routed back to the first column 145, via a suitable pump P1 or compressor.

The method can further comprise introducing a feed comprising gas stream 161 and portion 164 of liquid 162 into second column 170. As noted above, second column 170 can comprise a fractionation/distillation column. Second column 170 can comprise a deethanizer column configured to separate ethane and lighter components from the feed 165 to produce the second column bottoms stream 172. As noted hereinabove, second column 170 can be operated to provide a second column bottoms stream 172 as described hereinabove, for example comprising less than or equal to about 5 ppmw C2–. Second column 170 can be operated to provide a second column side stream 171 as described hereinabove, for example comprising from about 70 to about 99 vol % isobutane, from about 0 to about 10 vol % ethylene, and less than about 0.1 vol % hydrogen. Second column 170 can be operated to provide a second column overhead stream 173 as described hereinabove that minimizes loss of isobutane and ethylene.

The method can comprise recycling at least a portion 171' of the second column side stream 171. Recycling the at least the portion 171' of the second column side stream 171 can comprise introducing the at least the portion 171' of the second column side stream 171 to at least one of the one or more polymerization reactors 110 as a recycle diluent (e.g., isobutane) stream 171'. The recycle isobutane stream 171' can thus comprise greater than or equal to about 85, 90, or 95 weight percent (wt %) or from about 80, 85, or 90 to about 90, 95, or 99 vol % isobutane, greater than or equal to about 1, 5, or 10, or from about 0, 1, or 2 to about 3, 4, or 5 wt % olefins (e.g., ethylene), less than or equal to about 1, 0.1, or 0.01 ppmw or less than or equal to about 0.1 vol % hydrogen, or a combination thereof. The olefins can comprise ethylene, hexene, or a combination thereof.

The method can further comprise recycling at least a portion 172' of the substantially olefins-free isobutane stream 172 as a recycle olefins-free isobutane stream 172' to a catalyst pretreater 106' upstream of the one or more polymerization reactors 110, and using the catalyst pretreater 106' to form a catalyst slurry 106 comprising a polymerization catalyst 107 and the recycle olefins-free isobutane stream 172'. The second column bottoms stream 172 can be a substantially olefin-free isobutane stream 172 comprising greater than or equal to about 85, 90, or 95 weight percent (wt %), isobutane, less than or equal to about 50, 10, 5, or 1 ppmw olefins (e.g., ethylene), less than or equal to about 1, 0.1, or 0.01 ppmw, hydrogen, or a combination thereof.

Thus, in aspects, the method of this disclosure comprises separating feed 165 into a second column overhead stream 173, a second column side stream 171, and a second column bottom stream 172. In aspects, separating the feed 165 can generally comprise segregating parts of the feed 165 on the basis of various differences in physical or chemical properties between those parts. In aspects, separating the feed 165 into second column overhead stream 173, second column side stream 171, and second column bottoms stream 172 can generally comprise separating the feed 165 into a second column overhead stream 173 comprising ethylene, a second column side stream 171 comprising isobutane and ethylene and a low amount of hydrogen, and a second column bottom stream 172 comprising isobutane substantially free of olefins.

In aspects, separating the feed 165 into a second column overhead stream 173, a second column side stream 171, and a second column bottom stream 172 can be by any suitable device, apparatus, or process. Nonlimiting examples of such a suitable process include fractionation and distillation, and the like, as described herein.

In the aspect of FIG. 1A, separating the feed 165 into a second column overhead stream 173, a second column side stream 171, and a second column bottom stream 172 can comprise routing the feed stream 165 to the second column 170, which may be referred to as a lights column. The second column 170 can be similar in form and/or function to first column 145, or may be different, as appropriate for a product or process need or desire. For example, in aspects, the second column 170 may comprise a fractionation tower (or fractionation column). In alternative aspects, the second column 170 may comprise a distillation column (or distillation tower).

The second column 170 can be configured and/or sized provide for separation of a suitable volume of feed (e.g., the feed stream 165). For example, the second column 170 can be operated at a temperature in a range of from about 90° C. to about 15° C., alternatively, from about 80° C. to about 25° C., alternatively, from about 70 to about 35° C., and a pressure within about 10% of the pressure of first column 145, e.g., in a range of from about 14.7 psia to about 529.7 psia, alternatively, from about 15.7 psia to about 348 psia, alternatively, from about 85 psia to about 290 psia. The second column 170 can be configured and/or sized provide for separation of a suitable volume of feed 165. As will be appreciated by one of skill in the art viewing this disclosure, the feed 165 can remain and/or reside within second column 170 for any suitable amount of time as may be necessary to provide sufficient separation of the components of feed stream 165. In aspects, second column 170 can be provided with at least three outlets.

In aspects, the second column 170 can be configured and/or operated such that each of the second column overhead stream 173, the second column side stream 171, and the second column bottom stream 172 can comprise a desired portion, part, or subset of components of the feed 165. For example, as will be appreciated by one of skill in the art with the aid of this disclosure, the location of a particular stream outlet, the operating parameters of the second column 170, the composition of the feed 165, or combinations thereof may be manipulated such that a given stream may comprise a particular one or more components of the feed 165.

In aspects, second column overhead stream 173 can be characterized as comprising ethane and lighter gases (e.g., ethylene, ethane, methane, carbon dioxide, nitrogen, or hydrogen). For example, ethylene may be present in the second column overhead stream 173 in an amount from about 5% to about 65% by total weight of the second column overhead stream 173, alternatively from about 10% to about 55%, alternatively, from about 15% to about 45%. In aspects, the second column overhead stream 173 can be routed to further processing (e.g. catalytic cracking), routed to an ethylene plant, routed to storage, recycled (e.g., returned into the PPS I/I'), disposed of (e.g., flared), or employed in any otherwise suitable application or process.

As noted above, second column side stream 171 can be recycled. With reference to the aspect of FIGS. 1A and 1D, recycling the second column side stream 171 can comprise routing, for example, via a suitable pump or compressor, the second column side stream 171 back to and/or introducing the second column side stream 171 into the PPS I/I', for example, for reuse in a polymerization reaction of polymerization system 110. For example, in aspects, the second column side stream 171 can be introduced into the polymerization reactor(s) 110. Not intending to be bound by theory, because the second column side stream 171 can comprise ethylene, isobutane, and a low level of hydrogen, the second column side stream 171 can be introduced into polymerization reactor(s)/system 110 (e.g., a first polymerization reactor 110A, a second polymerization reactor 110B, or both). As such, the second column side stream 171 can serve as a source of isobutane and ethylene for a polymerization reaction. Recycling the second column side stream 171 can provide an efficient and/or cost-effective means of supplying isobutane for operation of the polymerization reaction process. Alternatively or additionally, second column side stream 171 can be routed to storage for subsequent use in a polymerization reaction or employed in any other suitable process.

In aspects, second column bottom stream 172 comprises $C_4$. In aspects, the second column bottom stream 172 can be free of olefins, alternatively, substantially free of olefins. For example, olefins can be present in the second column bottom stream 172 in an amount less than about 1.0% by total weight of the second column bottom stream 172, alternatively, less than about 0.5%, alternatively, less than about 0.1%.

As noted above, second column bottom stream 172 can be recycled. With reference to the aspect of FIGS. 1A and 1D, recycling the second column bottom stream 172 can comprise routing, for example, via a suitable pump or compressor, the second column bottom stream 172 back to and/or introducing the second column bottom stream 172 into the PPS I/I', for example, for reuse in a polymerization reaction of polymerization system 110. For example, in aspects, the second column bottom stream 172 can be combined with various other components (catalysts, cocatalysts, etc.) to form a catalyst slurry 106 that can be introduced into the polymerization reactor(s) 110. Not intending to be bound by theory, because the second column bottom stream 172 can comprise an olefin-free isobutane stream (alternatively, a substantially olefin-free, as disclosed above), the second column bottom stream 172 can be mixed with catalytic components (e.g., catalysts, cocatalysts, etc.) without the risk of unintended polymerization reactions (e.g., polymerization prior to introduction into the reactor). As such, the second column bottom stream 172 can serve as a source of olefin-free isobutane for a polymerization reaction. Recycling the second column bottom stream 172 (comprising olefin-free isobutane) can provide an efficient and/or cost-effective means of supplying isobutane for operation of the polymerization reaction process. Alternatively or additionally, second column bottom stream 172 can be routed to storage for subsequent use in a polymerization reaction or employed in any other suitable process.

In aspects, at least a portion of the second column bottom stream 172 can be returned to the second column 170. For example, in the example of FIG. 1A, a portion 172B of the second column bottom stream 172 is routed, via a second column reboiler R2, to the second column 170 for additional processing in second column 170, while portion 172A can be sent, for example, to an OFIC4 tank 190.

As discussed hereinabove with regard to the system, the method can further comprise operating the second column 170 at a second column pressure, and operating the first column 145 at a first column pressure, wherein the second column pressure is within about 10% of the first column pressure. The second column 170 pressure can be from about 120 psig to about 160 psig, for example, about 120, 130, 140, 150, or 160 psig.

In aspects of the method, a reboiler duty of a reboiler R2 associated with the second column 170 is less than a reboiler duty of a reboiler associated with a second column in a same method except wherein the second column is not operated at a second column pressure that is within about 10% of the first column pressure. In aspects, operation of the second column 170 at a pressure within about 10% of the pressure of the first column 145 enables the use of a diameter of the second column 170 to be less than a diameter of a second column utilized to provide a same separation in the same method (e.g., the same method except wherein the second column is not operated at a second column pressure that is within about 10% of the first column pressure).

In aspects, the method does not include compressing of the first column overhead stream 148, the gas stream 161, or the at least the portion 164 of the liquid stream 162 prior to introducing the gas stream 161 and the at least the portion 164 of the liquid stream 162 as feed 165 to the second column 170.

In aspects, the method of a disclosure does not include preheating of the feed 165 or components thereof (e.g., the gas stream 161, the liquid stream 162, the portion 164 of the liquid stream 162) between the second column 170 and the first column 145.

In aspects, the method includes extracting the second column side stream 171 at a liquid side draw stage SDS of the second column 170 that is separated from a feed stage FS of the second column 170 by more than 5, 6, 7, 8, 9, 10, 11, 12, 13, 14, or 15 theoretical or actual stages (trays), or by from about 3 to about 20, from about 5 to about 18, or from about 10 to about 15 theoretical or actual stages (trays). As noted hereinabove, the liquid side draw stage SDS is a stage from which or tray from immediately above which the second column 170 side stream 171 is withdrawn, and the feed stage FS is a stage to which or a tray immediately above which the second column 170 feed 165 is introduced to the second column 170.

In aspects, the method include operating the FGTS such that the second column side stream 171 as described hereinabove, for example comprising less than or equal to about 0.1 ppmw hydrogen, less than or equal to about 10 vol % ethylene, greater than or equal to about 90 vol % isobutane, or a combination thereof.

The method can comprise introducing the feed 165 to the second column 170 at subcooled or bubble point or super-heated conditions.

The method can further comprise maximizing an amount of ethylene in the second column side stream 171, while maintaining a concentration of hydrogen in the second column side stream 171 below a tolerance of the one or more polymerization reactor(s)/system 110 (e.g., at less than about 0.1, 0.5 or 1% ppmw $H_2$), and recycling at least a portion 171' of the second column side stream 171 to at least one of the one or more polymerization reactor(s)/system 110.

As noted above with reference to FIG. 1C, the one or more polymerization reactor(s)/system 110 can comprise an advanced dual loop reactor comprising a first polymerization reactor 110A upstream of a second polymerization reactor 110B. The first polymerization reactor 110A can be config-ured to produce a higher molecular weight polymer of a bimodal polymer, and the second polymerization reactor 110B can be configured to produce a lower molecular weight polymer of the bimodal polymer, wherein the higher molecular weight polymer has a higher average molecular weight than the lower molecular weight polymer. The method can include recycling at least a portion of the second column side stream 171 to the first polymerization reactor

110A, the second polymerization reactor 110B, or both. The one or more polymerization reactor(s)/system 110 (e.g., first polymerization reactor 110A, second polymerization reactor 110B) contain a polymerization catalyst 107, for example, such as described herein.

The method can further comprise condensing the second column overhead stream 173, and separating the condensed second column overhead stream 173 into a vent column overhead gas 186 and a vent column bottom liquid 187, returning at least a portion of the vent column bottom liquid 187 to the second column 170, and venting at least a portion of the vent column overhead gas 186.

The method can comprise operating the second column 170 at a second column pressure, and operating the first column 145 at a first column pressure, wherein the second column pressure is within about 10% of the first column pressure, wherein an amount of ethylene in the vent column overhead gas 186 is less than or equal to an amount of ethylene vented in a same method except wherein the second column 170 pressure is not within about 10% of the first column 145 pressure.

In aspects, a method (e.g., of treating a polymerization reactor effluent stream 111) comprises: recovering a polym-erization reactor effluent stream 111 from one or more polymerization reactor(s)/system 110; flashing the polymer-ization reactor effluent stream 111 (e.g., in flash system 100) to form a flash gas stream 140; separating, in a first column 145, the flash gas stream 140 into a first column overhead stream 148, a first column side stream 146, and a first column bottoms stream 147; separating the first column overhead stream 148 into a gas stream 161 and a liquid stream 162; introducing a feed 165 comprising the gas stream 161 and at least a portion 164 of the liquid stream 162 to a second column 170 to produce a second column overhead stream 173, a second column side stream 171, and a second column bottoms stream 172; and operating the second column 170 at a second column pressure, and operating the first column 145 at a first column pressure, wherein the second column 170 pressure is within about 10% of the first column 145 pressure.

In aspects, a method of this disclosure comprises: recov-ering a polymerization reactor effluent stream 111 from one or more polymerization reactor(s)/system 110; flashing (e.g., in a flash system 100) the polymerization reactor effluent stream 111 to form a flash gas stream 140; separating, in a first column 145, the flash gas stream 140 into a first column 145 overhead stream 148, a first column side stream 146, and a first column bottoms stream 147; separating the first column overhead stream 148 into a gas stream 161 and a liquid stream 162; introducing a feed 165 comprising the gas stream 161 and at least a portion 164 of the liquid stream 162 to a second column 170 to produce a second column overhead stream 173, a second column side stream 171, and a second column bottoms stream 172; and maximizing an amount of ethylene in the second column side stream 171, while maintaining a concentration of hydrogen in the second column side stream 171 below a tolerance of the one or more polymerization reactor(s)/system 110 (e.g., at less than about 0.1, 0.5, or 1% ppmw $H_2$), and recycling at least a portion 171' of the second column side stream 171 to at least one of the one or more polymerization reactor(s)/system 110.

In aspects, the systems and methods disclosed herein can have various advantages over prior art systems and/or pro-cesses. For example, by reducing the second column (e.g., deethanizer) operating pressure, increasing RIC4/OFIC4 ratio and using a colder and higher capacity refrigeration system 184, the herein disclosed system and method can provide significant advantages over conventional designs by reducing capital expenses (CAPEX) and operating expenses (OPEX) and improving plant operability. This savings can be attained, in aspects described herein, by eliminating the dehexanizer overhead compressor and associated pump and drum, feed economizer, and feed preheater, deethanizer condenser and accumulator/reflux pumps. Further savings can be realized by significantly reducing the sizes of the OFIC4 tank, treaters, high head OFIC4 reactor feed pump, deethanizer diameter and reboiler size. The savings is partially offset by a larger refrigeration package, larger RIC4 tank, pump and treaters, and a larger vent column system. During normal operation, improved deethanizer energy efficiency, and reduced ethylene loss in vent can, in aspects, lead to a significant net OPEX savings. In aspects, isobutane venting is increased due to lower second column operating pressures. The reduction of equipment count provided by the herein disclosed system can improve equipment reliability, process operability, and provide an efficient process design. A particularly notable benefit is eliminating the dehexanizer overhead compressor, which can provide a significant improvement on operability and debottlenecking due to numerous issues on commissioning and startup, performance, and reliability of said compressor.

Relative to the heavies/lights column setup used in direct recycle designs and conventional fractionation designs, differences between those two designs and the system and method described herein can include: (1) relative to the heavies/lights column for direct recycle plants, which can be operated at similar pressures, the proposed system and method can utilize larger columns that handle the entire reactor diluent stream, rather than just a portion thereof. Additionally, the deethanizer lights column can have an expanded section dedicated to the removal of hydrogen; and (2) relative to conventional dehexanizer/deethanizer columns, the herein disclosed system and method operate both columns at lower pressures (e.g., 120 to 140 psi, rather than 220 psig).

The absence of a compressive step between the first column 145 and the second column 170 can improve polymerization effluent stream processing systems and methods by reducing costs associated with equipment and processing, decreasing process complexity, or combinations thereof.

In addition to the elimination of various equipment facilitated by the system and method of this disclosure, the following equipment can also be modified by the herein disclosed PPS I/FGTS III: an OFIC4 tank 190 volume can be reduced (e.g., by about 2, 3, or 3.5 times), an OFIC4 pump size and head can be reduced allowing for use of a low head centrifugal pump, an OFIC4 treater size can be reduced, the deethanizer/second column 170 diameter and its reboiler R2 size can be reduced, an RIC4 tank 197 volume can be increased (e.g., by 1.5, 2, or 2.5 times), an RIC4 high-head pump size can be increased (e.g., by 1.5, 2, or 2.5 times), a refrigeration system 184 size can be increased (e.g., by 1.5, 2, or 2.5 times), or a combination thereof. The disclosed FGTS design can offer substantial savings on installed equipment cost comparing to conventional designs.

Furthermore, as noted herein, besides the CAPEX advantage, eliminating equipment particularly a dehexanizer overhead compressor, can provide significant improvement in operability and debottlenecking due to the challenge of operating such an overhead compressor.

In aspects, recycling the first column side stream 146 (e.g., hexene) back into the process can offset costs associated with hexene procurement, allow for optimized control of the hexene concentration at various points in the PPS (e.g., in the polymerization reaction), minimize the need to use fresh hexene, which may reduce one or more of raw material purchasing, transportation, and storage costs, avoid costs associated with hexene losses (e.g., regulatory fees), yield fewer waste products, or combinations thereof. In addition, recycling hexene (e.g., as the first column side stream 146), which may serve as a co-monomer in the polymerization process, may allow the quality and/or quantity of hexene routed to other points in the PPS (e.g., a polymerization reactor) to be independently controlled. Such independent control of hexene may lead to improved process control, the ability to optimize the process, and/or improved process efficiency, thereby reducing process costs and helping to minimize system complexity and/or downtime.

In aspects, the systems and methods disclosed herein can also allow for the separation of isobutane from heavy hydrocarbons present in the polymerization effluent stream (e.g., butane, pentane, hexane, hexene, heptane, etc.). Isolating isobutane from such heavier hydrocarbons can allow the isobutane routed to other points in the PPS (e.g., the catalyst pretreater 106', the polymerization system 110) to be independently controlled. Such independent control of the isobutane can lead to improved process control and/or process efficiency, thereby reducing process costs and helping to minimize system complexity and/or downtime.

In aspects, the systems and methods disclosed herein may allow for less energy consumption than other polymerization effluent stream treatment methods. For example, optimized process flows as disclosed herein may necessitate less energy for the process and/or may reduce the number of components, thereby leading to additional reductions in energy consumption.

In aspects, the systems and methods disclosed herein can provide a source of hexene-free isobutane (e.g., in second column bottom stream 172), which can facilitate responding to process fouling from the inadvertent introduction of, for example, hexene into the isobutane stream. In such aspects, the introduction of hexene-free isobutane can be employed to reverse the effects of hexene fouling of the isobutane stream through flushing or other remediation methods. Such usage of the hexene-free isobutane stream may, in turn, provide reduced downtime and thereby improve system uptime.

In aspects, overall system robustness can be another unexpected benefit of the systems and/or processes disclosed herein, and can be accompanied by the related capital and/or operating overhead reductions associated therewith. For example, such overall system robustness can be the result of a simplified process flow and/or the reduction in the number and complexity of components of such systems.

In aspects, a flash gas treatment system III of this disclosure can be utilized in a retrofit/debottleneck fractionation train in existing an existing polymer production system.

While the present disclosure has been illustrated and described in terms of particular apparatus and methods of use, it is apparent that equivalent techniques, components and constituents may be substituted for those shown, and other changes can be made within the scope of the present disclosure as defined by the appended claims.

EXAMPLES

The disclosure having been generally described, the following examples are given as particular aspect of the disclosure and to demonstrate the practice and advantages thereof. It is understood that the examples are given by way of illustration and is not intended to limit the specification or the claims in any manner.

Example 1

To demonstrate the operation of the systems and/or processes disclosed herein, a computerized commercial process simulator was employed to generate an output from a model in accordance with the systems and/or processes disclosed herein.

A Comparative System employed a second column (deethanizer column) operated at an elevated pressure relative to the first column (dehexanizer column). The higher pressures in the deethanizer column enabled its downstream vent column to operate at a relatively high pressure, which can decrease the concentration of isobutane in the overhead vent at the temperatures provided by the commonly available propane/propylene refrigerant, reducing isobutane losses.

The Comparative System design also included a liquid feed pre-heater to heat the liquid product of the upstream dehexanizer column up to its new bubble point following its increase in pressure from about 135 psig (bubble point of about 100° F.) to about 320 psig (bubble point of about 200° F.). The Comparative PPS also employed an economizing exchanger to exchanges waste heat from the deethanizer column bottoms with the liquid feed, reducing the amount of external heating supplied by the liquid feed pre-heater.

The deethanizer column of the Comparative System was designed such that approximately half of the total diluent flow exited from the sidedraw (e.g., deethanizer/second column side stream 171) containing some unreacted ethylene and potentially some hydrogen, while the remaining half exits the bottom of the column as olefin-free isobutane. The sidedraw recycle stream was recycled to the second polymerization reactor, where hydrogen could be tolerated, and the first reactor was fed olefin-free isobutane from the deethanizer bottom stream.

The comparative fractionation scheme has some drawbacks associated with the higher operating pressure of deethanizer column and 50/50 split of RIC4 and OFIC4 in the deethanizer. (1) The pressure differential between the dehexanizer and the deethanizer requires additional equipment, of which are not only to overcome the pressure differential (e.g., an intermediate compressor and pump between the dehexanizer and the deethanizer), but also to provide extra energy requirement associated with higher operating pressure (e.g., pre-heater and economizing exchanger). (2) Higher operating pressures in the deethanizer demands more duty from a deethanizer column reboiler due to the accompanying lower relative volatilities between components. (3) Producing a 50/50 split of RIC4 and OFIC4 in the deethanizer requires increasing storage vessel, pump, and treaters associated with OFIC4 in size to accommodate the large increase in flow, relative to systems in which olefin-free IC4 comprises less than 15 or 10% of the total diluent. (4) The 50/50 split of RIC4 and OFIC4 and bubble-point feed pre-heating also attribute to poor olefin efficiency.

The PPS I/I' of this disclosure provides recycle RIC4 171' that can be effectively used in polymerization reactor(s)/system 110 (e.g., first polymerization reactor 110A and/or second polymerization reactor 110B) via feed hydrogen metering and techniques used for analysis of hydrogen in the recycle isobutane stream 171'. Relative to the conventional Comparative System, deethanizer second column 170 operating pressure was reduced and the RIC4/OFIC4 ratio (e.g., the ratio of second column side draw stream 171 to second column bottoms stream 172) increased by the PPS of this disclosure.

In this example, Resin 1 was selected as one representative case because of its popularity, high $H_2$ feed requirements and ethane generation and high isobutane loss in vent, and Resin 2 was selected as another representative case because of its popularity, low $H_2$ feed requirements and ethane generation and low isobutane loss in vent.

A fractionation system, as depicted in FIG. 1B was selected for comparison with the Comparative System.

In Table 1 and Table 2, the proposed fractionation train design of FIG. 1B is compared to the results obtained for the comparative fractionation train design of the Comparative System described above, for Resin 1 at a common capacity.

TABLE 1

Comparisons Between PPS I and Comparative System on Deethanizer Second Column 170 for Resin 1

| 1 ppmw C2 = in OFIC4<br><0.01 ppmw H2 in RIC4<br>(Disclosed Design)<br><0.4 ppmw H2 in RIC4 | Deethanizer Column | |
| --- | --- | --- |
| (Comparative Design) | Disclosed System | Comparative System |
| No. of theoretical stages | 25 | 28 |
| Feed stage | #1 | #2 |
| Liquid sidedraw stage | #16 | #6 |
| Pressure (psig) (top/condenser/bottom) | 132[1]/Na/137 | 320/323/329 |
| Required feed preheater duty (MM Btu/h) | 0 | 1.6 |
| Required economizer duty (MM Btu/h) | 0 | 5.0 |
| Required condenser duty (MM Btu/h) | 0 | 4.2 |
| Required reboiler duty (MM Btu/h) | 2.1 | 5.9 |
| Min. dia. (ft) | 3.7 | 5.5 |
| RIC4/OFIC4 (kg/h) | 46,267/7,565 | 27,622/26,115 |

[1]Deethanizer pressure was determined by dehexanizer pressure and reasonable dP (3 psi) between dehexanizer/first column 145 and deethanizer/second column 170.

As shown in Table 1, in the FGTS III of this disclosure, operating pressure of the deethanizer column is reduced to 132 psig from 320 psig, and the ratio of RIC4/OFIC4 (e.g., second column side stream 171 to second column bottom stream 172) is increased to about 85/15 from about 50/50 in the Comparative System. These two changes enable (1) a more compact deethanizer second column 170 (e.g., 8 ft. shorter in deethanizer column height, 1.8 ft reduction in deethanizer column diameter); (2) less required equipment (eliminating compressor, feed preheater, economizing exchanger, condenser, condenser accumulator, and reflux pump); and (3) increased energy efficiency (e.g., eliminating cooling, 65% reduction in heating).

As shown in Table 2, in the disclosed system design, the operating pressure of vent column 185 is reduced to 117 psig from 305 psig, due to the decrease in the upstream (deethanizer second column 170) operating pressure. To counter the isobutane loss caused by lower operating pressure in deethanizer second column 170, a colder and higher capacity refrigeration system 184 can be included. The refrigeration system 184 temperature can be reduced (e.g., to about to −34° C.), and its duty a little more than doubled to reduce/minimize isobutane losses in vent column overhead gas stream 186.

The ethane (inert) venting rates are the same for both the disclosed FGTS III and the Comparative Design. In the disclosed design, the vent column 185 has a reduction in ethylene venting by about 140 kg/h, relative to that of the Comparative Design; however, an increase of isobutane venting of about 40 kg/h is seen with the disclosed FGTS III.

TABLE 2

Comparisons between PPS I and Comparative
System on Vent Column 185 for Resin 1

| | Vent Column 185 | |
| --- | --- | --- |
| | Disclosed System | Comparative System |
| No. of theoretical stages | 3 | 3 |
| Feed stage | #4 | #4 |
| Pressure (psig) (top/condenser/bottom) | 117/120/121 | 305/308/309 |
| Required condenser duty (MM Btu/h) | 1.2 @–34° C. | 0.5 @–25° C. |
| Min. dia. (ft) | 2.1 | 1.3 |
| Ethane venting rate (kg/h) | 121 | 121 |
| C2 = loss to vent (kg/h) | 686 | 825 |
| IC4 loss to vent (kg/h) | 82 | 39 |

In Table 3 and Table 4, the proposed new fractionation train design FGTS III is compared to the Comparative System fractionation train design for Resin 2 at a common capacity. As shown in Table 3, the proposed deethanizer second column 170 design offers very similar benefits for Resin 2 as for Resin 1.

Lower operating pressure of deethanizer second column 170 and higher RIC4/OFIC4 ratio (e.g., ratio of second column side stream 171 to second column bottom stream 172) enable (1) a more compact deethanizer second column 170 (e.g., 8 ft shorter in deethanizer second column 170 height, 2.2 ft reduction in deethanizer second column 170 diameter), (2) less required equipment (e.g., elimination of compressor, feed preheater, economizing exchanger, condenser, condenser accumulator, and reflux pump), and (3) increased energy efficiency (e.g., eliminating cooling, 64% reduction in heating).

TABLE 3

Comparisons Between PPS I and Comparative System
on Deethanizer Second Column 170 for Resin 2

1 ppmw C2 = in OFIC4
<0.01 ppmw H2 in RIC4
(Disclosed Design)
<0.4 ppmw H2 in RIC4

| (Comparative Design) | Deethanizer Column | |
| --- | --- | --- |
| | Disclosed System | Comparative System |
| No. of theoretical stages | 25 | 28 |
| Feed stage | #1 | #2 |
| Liquid sidedraw stage | #16 | #6 |
| Pressure (psig) (top/condenser/bottom) | 132/Na/137 | 320/323/329 |
| Required feed preheater duty (MM Btu/h) | 0 | 1.8 |
| Required economizer duty (MM Btu/h) | 0 | 5.6 |
| Required condenser duty (MM Btu/h) | 0 | 4.9 |
| Required reboiler duty (MM Btu/h) | 2.5 | 6.9 |
| Min. dia. (ft) | 3.9 | 6.1 |
| RIC4/OFIC4 (kg/h) | 50,514/7,910 | 28,949/29,329 |

As shown in Table 4, similar to the Resin 1 case, the operating pressure of vent column 185 is reduced, a colder and higher capacity refrigeration system 184 can be included in the proposed design to counter the isobutane loss caused by lower operating pressure in deethanizer second column 170, the refrigeration system 184 temperature was reduced to –36° C. for this Resin 2 Example, and its duty was doubled, the ethane (inert) venting rates are the same for both Disclosed System (PPS I) and the Comparative System. The vent column 185 of the herein disclosed PPS I has a reduction in ethylene venting by about 200 kg/h, however, an increase of isobutane venting by about 50 kg/h was seen in the Disclosed System relative to the Comparative System.

TABLE 4

Comparisons between PPS I and Comparative
System on Vent Column 185 for Resin 2

| | Vent Column 185 | |
| --- | --- | --- |
| | Disclosed System | Comparative System |
| No. of theoretical stages | 3 | 3 |
| Feed stage | #4 | #4 |
| Pressure (psig) (top/condenser/bottom) | 117/120/121 | 305/308/309 |
| Required condenser duty (MM Btu/h) | 1.1 @–36° C. | 0.6 @–25° C. |
| Min. dia. (ft) | 2.1 | 1.5 |
| Ethane venting rate (kg/h) | 18 | 18 |
| C2 = loss to vent (kg/h) | 1196 | 1395 |
| IC4 loss to vent (kg/h) | 54 | 5 |

Example 2

Figure 3:
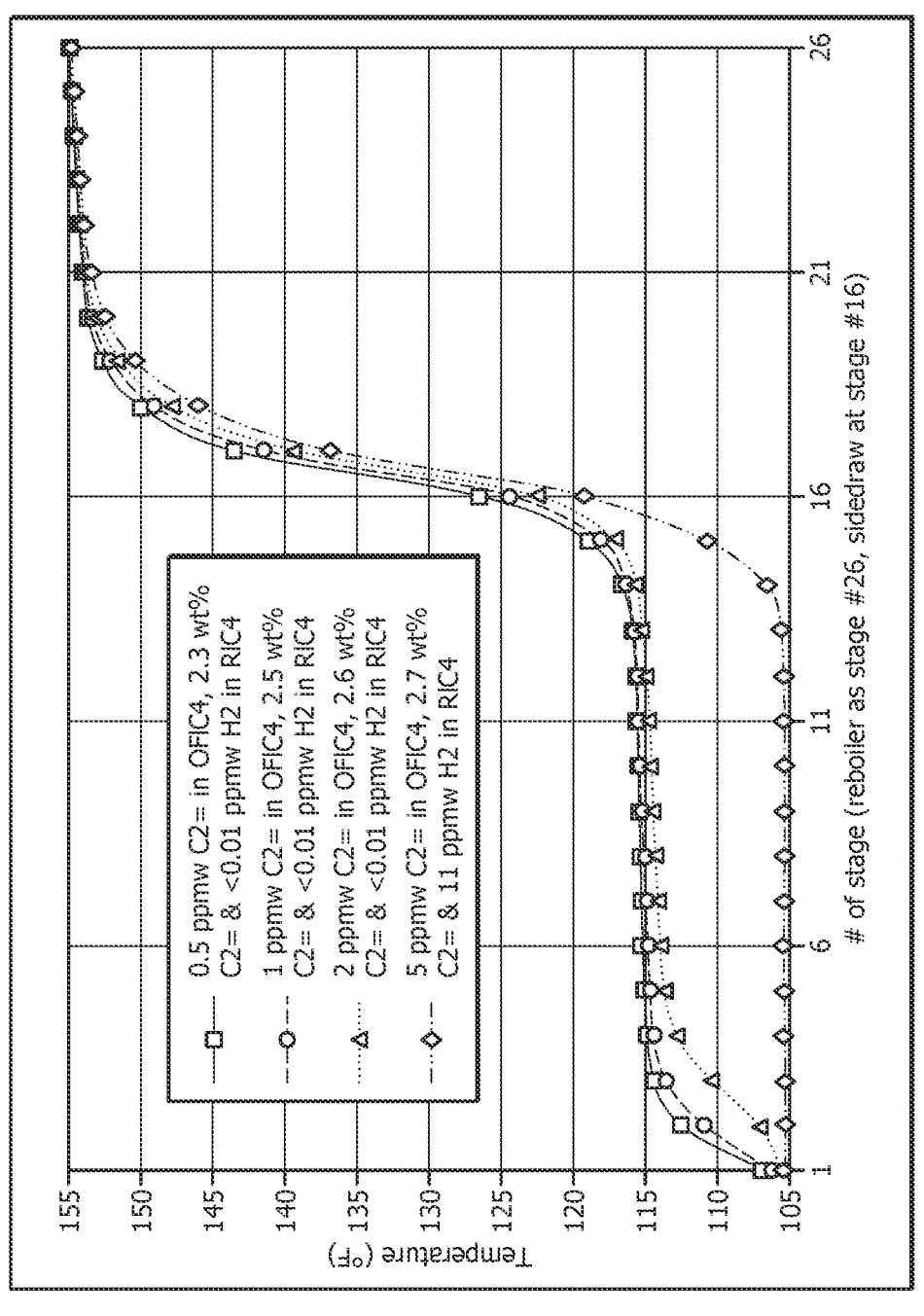
FIG. 3 shows deethanizer temperature profiles obtained with different amounts of ethylene in a substantially olefins-free isobutane stream (OFIC4) and ethylene and hydrogen in a recycle isobutane stream (RIC4)
Figure 4:
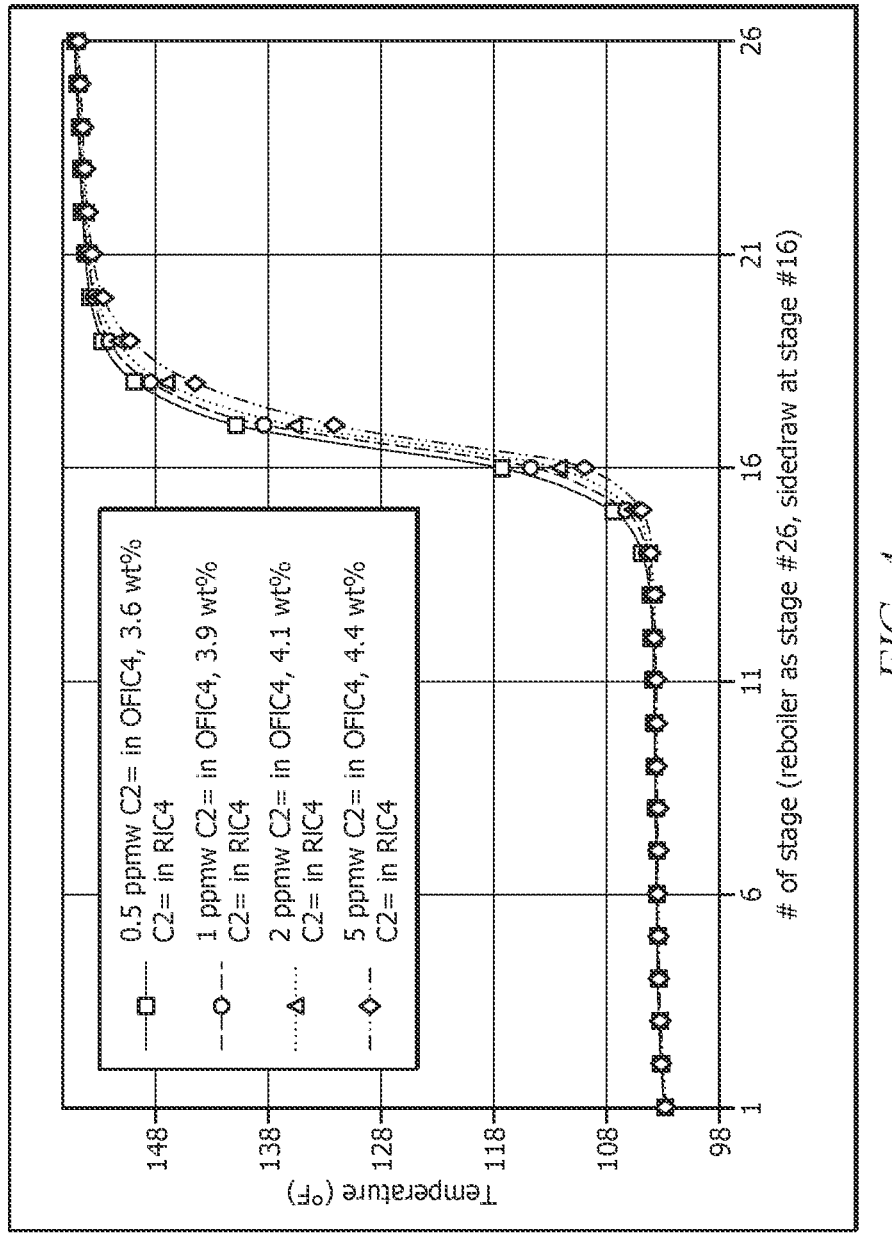
FIG. 4 shows deethanizer temperature profiles obtained with different amounts of ethylene in the substantially olefins-free isobutane stream (OFIC4) and ethylene in the recycle isobutane stream (RIC4)

Deethanizer second column 170 temperature profiles are shown in FIG. 3 and FIG. 4 for Resin 1 and Resin 2, respectively. For each resin, four lines were modeled to depict one on-spec case (e.g., 1 ppmw ethylene (C2=) in OFIC4), one deviation case (e.g., 0.5 ppmw C2= in OFIC4), and two off-spec cases (e.g., 2 ppmw and 5 ppmw C2= in OFIC4). The sidedraw location is determined such that H2 in RIC4 on-spec (e.g., less than or equal to 1% ppmw) is guaranteed when C2= in OFIC4 specification is met (e.g., 1 ppmw).

The sidedraw location (SDS, FIG. 2) was determined by case with high H2 presence, e.g., Resin 1. The sidedraw location becomes very conservative for case with low H2 presence, e.g., Resin 2. As shown in FIG. 4 for Resin 2, this conservative sidedraw location, even with C2= in OFIC4 off-spec, H2 in RIC4 is still well below spec value.

The control objective was to maintain (1) temperatures of sidedraw stage and the two stages right below hot enough to reject C2= from liquid, and (2) temperatures of the stages above second column side stream 171 sidedraw hot enough to reject H2 from liquid; the control handle is the reboiler R2 steam 174.

The temperature deltas are greatest at sidedraw location (stage #16), and the 1 stage above and below the SDS. With the higher deltas at these stages, these locations can be best for tray tower control. As C2= and H2 make their way down the tower, the tray temperature TI can sense the change with respect to time and the temperature controller (TC) can adjust reboiler R2 steam 174 as required.

Based on the temperature profile and control loop timing, one TI can be placed at stage #17 (the second actual tray below the sidedraw tray) for column temperature control of OFIC4 for both Resin 1 and Resin 2. On the other hand, if the sidedraw stage (stage #16) temperature were utilized as the control temperature of RIC4, timing may be an issue for this control loop. The moment the temperature difference is sensed, and the reboiler R2 steam 174 adjusted, H2 has already made it to RIC4. For better control loop timing, one TI can be placed at stage #4 or stage #5 (e.g., the #7 or #8 actual tray from top) for column temperature control of RIC4 for Resin 1.

As shown in FIG. 4, for Resin 2, no/limited temperature delta exists at stages above sidedraw location SDS, because H2 in RIC4 concentrations are always well below spec value for all cases. RIC4 is more likely off-spec in Resin 1 case, and highly unlikely off-spec in Resin 2 case, as noted above.

Figure 5:
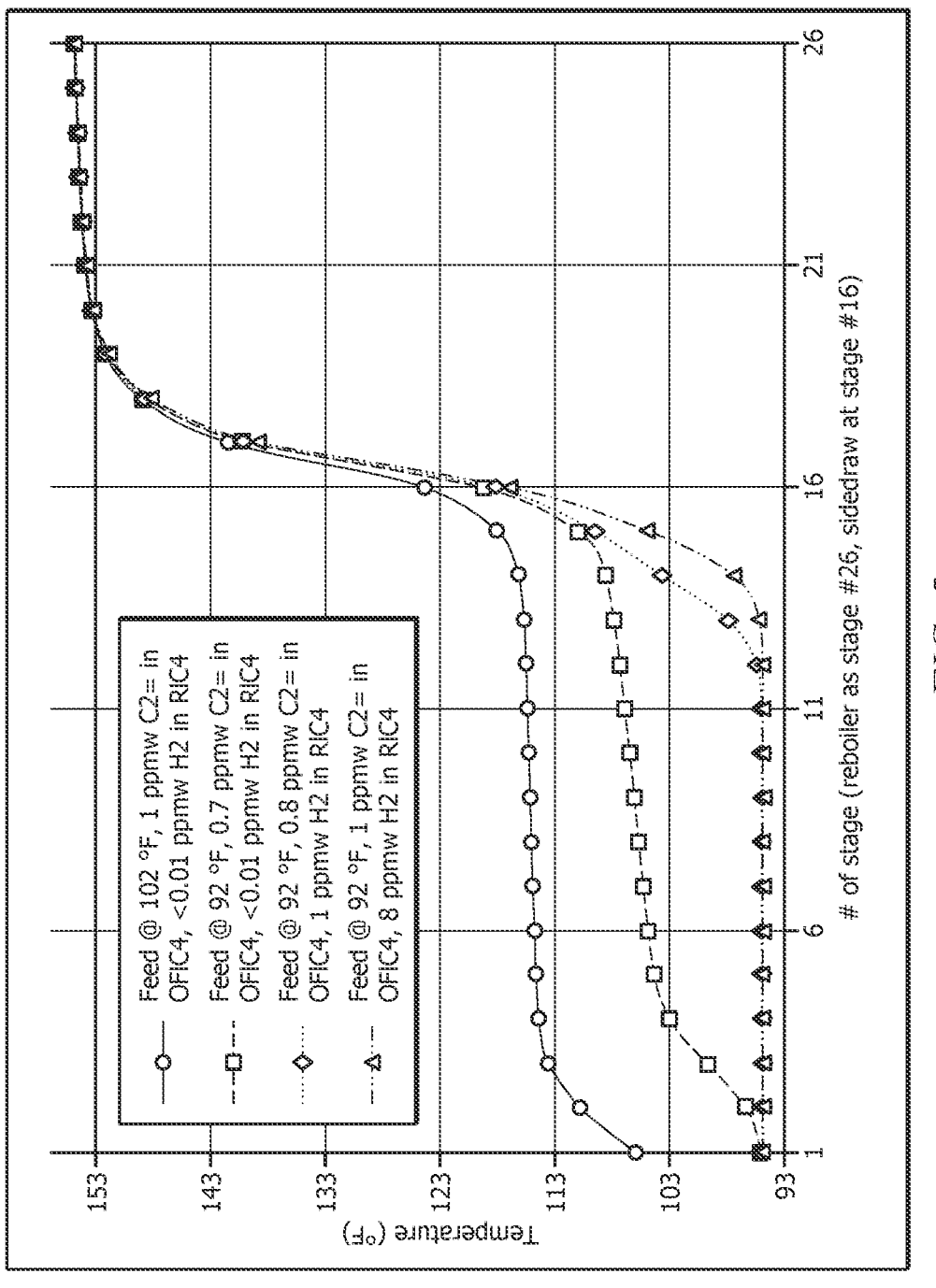
FIG. 5 shows deethanizer temperature profiles for 10° F. (colder) deviation on feed at different amounts of ethylene in the substantially olefins-free isobutane stream (OFIC4) and hydrogen in the recycle isobutane stream (RIC4).

For Resin 1, as shown in FIG. 3, low temperature (bottom, diamond line) in deethanizer second column 170 top section leads to high (off-spec) H2 concentration in RIC4 stream 171. In operation, such a low temperature profile can be caused by feed temperature deviation (colder). In FIG. 5, with a colder feed (92° F.) to deethanizer second column 170, top section temperatures become lower for all cases (square, diamond, triangle lines) compared to reference case (circles line, Feed@ 102° F.). As shown in triangles line, although OFIC4 is on-spec, the H2 in RIC4 is off-spec (8 ppmw). To reduce the H2 in RIC4, top section temperature profiles can be lifted (squares and triangles lines) by increasing reboiler R2 duty, which also results in reduction C2= in OFIC4 172.

Based on characteristics of FIG. 3 and FIG. 5, besides direct temperature control of RIC4 171 for Resin 1, alternatively differential temperature control strategy can be utilized to control RIC4 171 for Resin 1. For one differential temperature control scheme, the feed temperature to the column (T$_{feed}$) and the temperature at stage #4 (T4) can be measured. The delta between these two (dT=T4−T$_{feed}$) can be calculated. This dT value could be controlled at a constant value, e.g., 10° F. to fix the location of the upper wave and result in the <0.01 ppmw H2 in RIC4 171, as shown in squares/circles/triangles lines in FIG. 3 and squares line in FIG. 5. This control strategy can provide a quicker and more responsive control for feed temperature deviation, in aspects.

For another differential temperature control scheme, the temperature at stage #24 (T24) and the temperature at stage #5 (T5) can be measured. The delta between these two (dT=T24−T5) can then be calculated. This dT value could be controlled in a certain range, e.g., 40-50° F. to fix the location of the upper wave and result in the <0.01 ppmw H2 in RIC4 171, as shown in squares/circles/triangles lines in FIG. 3 and squares line in FIG. 5. This control strategy can provide a pressure-compensated temperature control. The temperature near the bottom (e.g., T24) can be chosen as a reference because temperature is relatively constant and insensitive to composition near the bottom of deethanizer second column 170, as shown in FIG. 3 and FIG. 5.

ADDITIONAL DISCLOSURE

The particular aspects disclosed above are illustrative only, as the present disclosure can be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative aspects disclosed above can be altered or modified and all such variations are considered within the scope and spirit of the present disclosure. Alternative aspects that result from combining, integrating, and/or omitting features of the aspect(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above can vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted. The term "about" (e.g., "about 10") can indicate ±10% (e.g., 9 to 11), and includes equal to (e.g., equal to 10), in aspects. "Substantially" equal to a value can include within 5, 4, 3, 2, or 1% or equal to the value, in aspects.

The following are non-limiting, specific aspects in accordance with the present disclosure:

In a first aspect, method (of treating a polymerization reactor effluent) comprises: recovering a polymerization reactor effluent stream from one or more polymerization reactors; flashing the polymerization reactor effluent stream to form a flash gas stream; separating, in a first column, the flash gas stream into a first column overhead stream, a first column side stream, and a first column bottoms stream; separating the first column overhead stream into a gas stream and a liquid stream; and introducing a feed comprising the gas stream and at least a portion of the liquid stream to a second column to produce a second column overhead stream, a second column side stream, and a second column bottoms stream, wherein the second column bottoms stream has a second column bottoms flow rate of isobutane and the second column side stream has a second column side stream flow rate of isobutane, wherein a total flow rate of isobutane comprises the second column bottoms stream flow rate and the second column side stream flow rate, and wherein the second column bottoms stream flow rate comprises less than or equal to about 15, 20, or 25 volume percent (vol %) of the total flow rate and the second column side stream flow rate comprises greater than or equal to about 85, 80, or 75 vol % of the total flow rate.

A second aspect can comprise the method of the first aspect further comprising returning at least a portion of the first column side stream to at least one of the one or more polymerization reactors.

A third aspect can include the method of the first or the second aspect, wherein the first column comprises a fractionation/distillation column.

A fourth aspect can comprise the method of the third aspect, wherein the first column comprises a dehexanizer column configured to separate hexane and heavier components from the flash gas stream to provide the first column overhead stream, wherein the first column overhear stream comprises less than or equal to about 10, 5, or 1 ppmw C6+, wherein the first column side stream comprises from about 80, 85, or 90 to about 95, 98, 99, or 100 vol. % hexene (e.g., from about 60 to 100 vol % hexene), and wherein the first column bottoms stream comprises primarily C6+ (e.g., hexane, oils, oligomers, or a combination thereof).

A fifth aspect can include the method of any one of the first to fourth aspects, wherein separating the first column top stream is effected in an accumulator.

A sixth aspect can include the method of any one of the first to fifth aspects, wherein the second column comprises a fractionation/distillation column.

A seventh aspect can include the method of the sixth aspect, wherein the second column comprises a deethanizer column configured to separate ethane and lighter components from the feed to produce the second column bottoms stream, wherein the second column bottoms stream comprises less than or equal to about 10, 5, or 1 ppmw C2−, wherein the second column side stream comprises from about 85, 90, or 92 to about 95, 98, or 99 wt % isobutane, from about 1, 2, or 3 to about 4, 5, 6, 7, 8, 9, or 10 vol. % ethylene, and less than or equal to about 0.1 ppmw hydrogen, and wherein the second column overhead stream maximizes ethylene and isobutane losses.

An eighth aspect can include the method of any one of the first to seventh aspects further comprising recycling at least a portion of the second column side stream.

A ninth aspect can include the method of the eighth aspect, wherein recycling the at least the portion of the second column side stream further comprises introducing the at least the portion of the second column side stream to at least one of the one or more polymerization reactors as a recycle isobutane stream.

A tenth aspect can include the method of the ninth aspect, wherein the recycle isobutane stream comprises greater than or equal to about 10 volume percent (vol %) isobutane, less than or equal to about 10 vol % olefins (e.g., ethylene), less than or equal to about 0.1 ppmw hydrogen, or a combination thereof.

An eleventh aspect can include the method of the tenth aspect, wherein the olefins comprise ethylene, hexene, or a combination thereof.

A twelfth aspect can include the method of any one of the first to eleventh aspects, wherein the second column bottoms stream is a substantially olefin-free isobutane stream comprising greater than or equal to about 95, 96, 97, 98, or 99 volume percent (vol %), less than or equal to about 50 ppmw olefins (e.g., ethylene), less than or equal to about 0.1 ppmw hydrogen, or a combination thereof.

A thirteenth aspect can include the method of the twelfth aspect, wherein the olefins comprise ethylene, hexene, or a combination thereof.

A fourteenth aspect can include the method of the twelfth or thirteenth aspect further comprising recycling at least a portion of the substantially olefins-free isobutane stream as a recycle olefins-free isobutane stream to a catalyst pretreater upstream of the one or more polymerization reactors, and using the catalyst pretreater to form a catalyst slurry comprising a polymerization catalyst and the recycle olefins-free isobutane stream.

A fifteenth aspect can include the method of any one of the first to fourteenth aspects further comprising operating the second column at a second column pressure, and operating the first column at a first column pressure, wherein the second column pressure is within about 10, 15, or 20% of the first column pressure.

A sixteenth aspect can include the method of the fifteenth aspect, wherein the second column pressure is from about 110 psig to about 160 psig.

A seventeenth aspect can include the method of the sixteenth aspect, wherein the second column pressure is about 120 psig.

An eighteenth aspect can include the method of the seventeenth aspect, wherein a reboiler duty of a reboiler associated with the second column is less than a reboiler duty of a reboiler associated with a second column in a same method except wherein the second column is not operated at a second column pressure that is within about 10% of the first column pressure.

A nineteenth aspect can include the method of the seventeenth or eighteenth aspect, wherein a diameter of the second column is less than a diameter of the second column utilized to provide a same separation in the same method.

A twentieth aspect can include the method of any one of the first to nineteenth aspects, comprising no compressing of the first column overhead stream, the gas stream, or the at least the portion of the liquid stream prior to introducing the gas stream and the at least the portion of the liquid stream as feed to the second column.

A twenty first aspect can include the method of any one of the first to twentieth aspects, comprising no preheating of the feed or components thereof (e.g., the gas stream, the liquid stream) between the second column and the first column.

A twenty second aspect can include the method of any one of the first to twenty first aspects, wherein a liquid side draw stage of the second column is separated from a feed stage of the second column by more than 5, 6, 7, 8, 9, 10, 11, 12, 13, 14, or 15 theoretical or actual stages (trays), or by from about 3 to about 20, from about 5 to about 18, or from about 10 to about 15 theoretical or actual stages (trays), wherein the liquid side draw stage is a stage from which or tray from immediately above which the second column side stream is withdrawn, and wherein the feed stage is a stage to which or a tray immediately above which the second column feed is introduced to the second column.

A twenty third aspect can include the method of any one of the first to twenty second aspects, wherein the second column side stream comprises less than or equal to about 1, 0.1, or 0.01 ppmw, less than or equal to about 1, 2, 3, 4, 5, 6, 7, 8, 9, or 10 weight percent (wt %) ethylene, greater than or equal to about 80, 85, or 90 weight percent (wt %) isobutane, or a combination thereof.

A twenty fourth aspect can include the method of any one of the first to twenty third aspects further comprising maximizing an amount of ethylene in the second column side stream, while maintaining a concentration of hydrogen in the second column side stream below a tolerance of the one or more polymerization reactors (e.g., at less than about 1, 0.1, or 0.01 ppmw $H_2$), and recycling at least a portion of the second column side stream to at least one of the one or more polymerization reactors.

A twenty fifth aspect can include the method of any one of the first to twenty fourth aspects, wherein the one or more polymerization reactors comprise an advanced dual loop reactor comprising a first polymerization reactor upstream of a second polymerization reactor.

A twenty sixth aspect can include the method of the twenty fifth aspect, wherein the first polymerization reactor is configured to produce a higher molecular weight polymer of a bimodal polymer, and wherein the second polymerization reactor is configured to produce a lower molecular weight polymer of the bimodal polymer, wherein the higher molecular weight polymer has a higher average molecular weight than the lower molecular weight polymer.

A twenty seventh aspect can include the method of the twenty fifth or twenty sixth aspect further comprising recycling at least a portion of the second column side stream to the first polymerization reactor, the second polymerization reactor, or both.

A twenty eighth aspect can include the method of any one of the first to twenty seventh aspects, wherein the one or more polymerization reactors contain a polymerization catalyst.

A twenty ninth aspect can include the method of any one of the first to twenty eighth aspects further comprising condensing the second column overhead stream, and separating the condensed second column overhead stream into a second column overhead gas and a second column overhead liquid, returning at least a portion of the second column overhead liquid to the second column, and venting at least a portion of the second column overhead gas.

A thirtieth aspect can include the method of the twenty ninth aspect further comprising operating the second column at a second column pressure, and operating the first column at a first column pressure, wherein the second column pressure is within about 10% of the first column pressure, wherein an amount of ethylene in the second column overhead gas is less than or equal to an amount of ethylene vented in a same method except wherein the second column pressure is not within about 10% of the first column pressure.

In a thirty first aspect, a method (of treating a polymerization reactor effluent) comprises: recovering a polymerization reactor effluent stream from one or more polymerization reactors; flashing the polymerization reactor effluent stream to form a flash gas stream; separating, in a first column, the flash gas stream into a first column overhead stream, a first column side stream, and a first column bottoms stream; separating the first column overhead stream into a gas stream and a liquid stream; introducing a feed comprising the gas stream and at least a portion of the liquid stream to a second column to produce a second column overhead stream, a second column side stream, and a second column bottoms stream; and operating the second column at a second column pressure, and operating the first column at a first column pressure, wherein the second column pressure is within about 10% of the first column pressure.

In a thirty second aspect, a method (of treating a polymerization reactor effluent) comprises: recovering a polymerization reactor effluent stream from one or more polymerization reactors; flashing the polymerization reactor effluent stream to form a flash gas stream; separating, in a first column, the flash gas stream into a first column overhead stream, a first column side stream, and a first column bottoms stream; separating the first column overhead stream into a gas stream and a liquid stream; introducing a feed comprising the gas stream and at least a portion of the liquid stream to a second column to produce a second column overhead stream, a second column side stream, and a second column bottoms stream; and maximizing an amount of ethylene in the second column side stream, while maintaining a concentration of hydrogen in the second column side stream below a tolerance of the one or more polymerization reactors (e.g., at less than about 1, 0.1, or 0.01 ppmw $H_2$), and recycling at least a portion of the second column side stream to at least one of the one or more polymerization reactors.

In a thirty third aspect, a system (of treating a polymerization reactor effluent, the system) comprises: one or more polymerization reactors configured to produce a polymerization reactor effluent stream; flash apparatus configured for flashing the polymerization reactor effluent stream to form a flash gas stream; a first column configured to separate the flash gas stream into a first column overhead stream, a first column side stream, and a first column bottoms stream; a liquid/vapor separator configured for separating the first column overhead stream into a gas stream and a liquid stream; and a second column configured to receive a feed comprising the gas stream and at least a portion of the liquid stream and separate the feed to produce a second column overhead stream, a second column side stream, and a second column bottoms stream, wherein a second column bottoms outlet line is configured for a second column bottoms stream flow rate of isobutane and a second column side stream is configured for a second column side stream flow rate of isobutane, wherein a total flow rate of isobutane comprises the bottoms stream flow rate and the side stream flow rate, and wherein the bottoms stream flow rate comprises less than or equal to about 15 volume percent (vol. %) of the total flow rate and the side stream flow rate comprises greater than or equal to about 85 vol. % of the total flow rate.

A thirty fourth aspect can include the system of the thirty third aspect, comprising no compressor between the first column and the second column.

A thirty fifth aspect can include the system of the thirty third or thirty fourth aspect, configured for operation of the second column at a pressure within about 10% of a pressure at which the first column is operated.

A thirty sixth aspect can include the system of any one of the thirty third to thirty fifth aspects, wherein the first column, the second column, or both comprise a fractionation/distillation column.

A thirty seventh aspect can include the system of the thirty sixth aspect, wherein the first column comprises a dehexanizer column configured to separate hexane and heavier components from the flash gas stream to provide the first column overhead stream, wherein the first column overhead stream comprises less than or equal to about 10, 5, or 1 ppmw C6+ (e.g., compounds containing 6 or more carbon atoms), wherein the first column side stream comprises from about 85, 90, or 95 to about 95, 98, 99, or 100 wt % hexene, and wherein the first column bottoms stream comprises primarily C6+ (e.g., compounds containing six or more carbon atoms; such as hexane, oils, oligomers, or a combination thereof).

A thirty eighth aspect can include the system of any one of the thirty third to thirty seventh aspects, wherein the liquid/vapor separator comprises an accumulator.

A thirty ninth aspect can include the system of any one of the thirty third to thirty eighth aspects, wherein the second column comprises a deethanizer column configured to separate ethane and lighter components from the feed to produce the second column bottoms stream, wherein the second column bottoms stream comprises less than or equal to about 10, 5, or 1 ppmw C2− (e.g., compounds having two or fewer carbon atoms) wherein the second column side stream comprises from about 85, 90, or 92 to about 95, 98, 99, or 100 wt % isobutane, from about 1, 2, 3, 4, or 5 to about 4, 5, 6, 7, 8, 9, or 10 wt % ethylene, and from about 1, 0.1, or 0.01 to about 0.1, 0.01, or 0.001 ppmw hydrogen, and wherein the second column overhead stream comprises from about 70, 65, or 60 to about 45, 50, or 55 wt %, or less than or equal to about 70, 65, or 60 wt % isobutane, from about 10, 15, or 20 to about 55, 50, or 45 wt. %, or less than or equal to about 55, 50, or 45 wt. % ethylene.

A fortieth aspect can include the system of any one of the thirty third to thirty ninth aspects further comprising a recycle path for recycling at least a portion of the second column side stream.

A forty first aspect can include the system of the fortieth aspect, wherein the recycle path introduces the at least the portion of the second column side stream to at least one of the one or more polymerization reactors as a recycle isobutane stream.

A forty second aspect can include the system of the forty first aspect, configured such that the recycle isobutane stream comprises greater than or equal to about 80, 85, or 90 weight percent (wt %) or from about 85, 90, or 92 to about 95, 98, or 99 isobutane, greater than or equal to about 1, 2, 3, 4, or 5, or from about 11, 2, 3, 4, or 5 to about 10, 9, 8, 7, or 6 wt % olefins (e.g., ethylene), less than or equal to about 1, 0.1, or 0.01 ppmw, or from about 1, 0.1, or 0.01 to about 0.1, 0.01, or 0.001 ppmw hydrogen, or a combination thereof.

A forty third aspect can include the system of the forty second aspect, wherein the olefins comprise ethylene, hexene, or a combination thereof.

A forty fourth aspect can include the system of any one of the thirty third to forty third aspects, wherein the second column bottoms stream is a substantially olefin-free isobutane stream comprising greater than or equal to about 85, 90, or 95 weight percent (wt %), or from about 85, 90, or 95 to about 97, 98, or 99 wt % isobutane, less than or equal to about 50, 10, or 1 wt %, or from about 50, 10, or 1 to about 5, 1, or 0.1 ppmw olefins (e.g., ethylene), less than or equal to about 0.1, 0.01, or 0.001 ppmw hydrogen, or a combination thereof.

A forty fifth aspect can include the system of the forty fourth aspect, wherein the olefins comprise ethylene, hexene, or a combination thereof.

A forty sixth aspect can include the system of the forty fourth or forty fifth aspect further comprising a catalyst pretreater upstream of the one or more polymerization reactors, and a recycle path for recycling at least a portion of the substantially olefins-free isobutane stream from the second column as a recycle olefins-free isobutane stream to the catalyst pretreater, wherein the catalyst pretreater is configured to produce a catalyst slurry comprising a polymerization catalyst and the recycle olefins-free isobutane stream.

A forty seventh aspect can include the system of any one of the thirty third to forty sixth aspects, wherein the second column is in operation at a second column pressure and the first column is in operation at a first column pressure, wherein the second column pressure is within about 10% of the first column pressure.

A forty eighth aspect can include the system of the forty seventh aspect, wherein the second column pressure is from about 110 psig to about 160 psig.

A forty ninth aspect can include the system of the forty eighth aspect, wherein the second column pressure is about 120 psig.

A fiftieth aspect can include the system of any one of the forty seventh to forty ninth aspects further comprising a reboiler associated with the second column, wherein a reboiler duty of the reboiler associated with the second column is less than a reboiler duty of a reboiler associated with a second column in a same system except wherein the second column is not operated at a second column pressure that is within about 10% of the first column pressure.

A fifty first aspect can include the system of the fiftieth aspect, wherein a diameter of the second column is less than a diameter of the second column utilized to provide a same separation in the same system.

A fifty second aspect can include the system of any one of the thirty third to fifty first aspects, comprising no compressor for compressing of the first column overhead stream, the gas stream, or the at least the portion of the liquid stream prior to introduction of the gas stream and the at least the portion of the liquid stream as feed to the second column.

A fifty third aspect can include the system of any one of the thirty third to fifty second aspects, comprising no preheater for preheating of the feed or components thereof (e.g., the gas stream, the liquid stream) between the second column and the first column.

A fifty fourth aspect can include the system of any one of the thirty third to fifty third aspects, wherein a liquid side draw stage of the second column is separated from a feed stage of the second column by more than 5, 6, 7, 8, 9, 10, 11, 12, 13, 14, or 15 theoretical or actual stages (trays), or by from about 3 to about 20, from about 5 to about 18, or from about 10 to about 15 theoretical or actual stages (trays), wherein the liquid side draw stage is a stage from which or tray from immediately above which the second column side stream is withdrawn, and wherein the feed stage is a stage to which or a tray immediately above which the second column feed is introduced to the second column.

A fifty fifth aspect can include the system of any one of the thirty third to fifty fourth aspects, configured to produce the second column side stream comprising less than or equal to about 1, 0.1, or 0.01 ppmw, or from about 1, 0.1, or 0.01 to about 0.1, 0.01, or 0.001 ppmw hydrogen, greater than or equal to about 1, 2, or 3 wt percent (wt %), or from about 1, 2, 3, 4, or 5 to about 5, 6, 7, 8, 9, or 10 weight percent (wt %) ethylene, greater than or equal to about 80, 85, or 90 wt %, or from about 80, 85, or 90 to about 95, 97, or 99 weight percent (wt %) isobutane, or a combination thereof.

A fifty sixth aspect can include the system of anyone of the thirty third to fifty fifth aspects configured for introducing the feed (e.g., having one or more feed inlets 166) to the second column at a feed location to minimize ethylene and isobutane losses.

A fifty seventh aspect can include the system of any one of the thirty third to fifty sixth aspects configured for maximizing an amount of ethylene in the second column side stream, while maintaining a concentration of hydrogen in the second column side stream below a tolerance of the one or more polymerization reactors (e.g., at less than about 10.1, 0.1, or 0.01 ppmw $H_2$), and further comprising a recycle path for recycling at least a portion of the second column side stream to at least one of the one or more polymerization reactors.

A fifty eighth aspect can include the system of any one of the thirty third to fifty seventh aspects, wherein the one or more polymerization reactors comprise an advanced dual loop reactor comprising a first polymerization reactor upstream of a second polymerization reactor.

A fifty ninth aspect can include the system of the fifty eighth aspect, wherein the first polymerization reactor is configured to produce a higher molecular weight polymer of a bimodal polymer, and wherein the second polymerization reactor is configured to produce a lower molecular weight polymer of the bimodal polymer, wherein the higher molecular weight polymer has a higher average molecular weight than the lower molecular weight polymer.

A sixtieth aspect can include the system of the fifty eighth or fifty ninth aspect further comprising a recycle path for recycling at least a portion of the second column side stream to the first polymerization reactor, the second polymerization reactor, or both.

A sixty first aspect can include the system of any one of the thirty third to sixtieth aspects, wherein the one or more polymerization reactors contain a polymerization catalyst.

A sixty second aspect can include the system of any one of the thirty third to sixty first aspects further comprising a condenser for condensing the second column overhead stream, and a separating the condensed second column overhead stream into a second column overhead gas and a second column overhead liquid, a reflux line for returning at least a portion of the second column overhead liquid to the second column, and a vent for venting at least a portion of the second column overhead gas.

A sixty third aspect can include the system of the sixty second aspect, wherein the second column is operating at a second column operating pressure, and the first column is operating at a first column operating pressure, wherein the second column operating pressure is within about 10% of the first column operating pressure, and wherein an amount of ethylene in the second column overhead gas being vented is less than or equal to an amount of ethylene vented in a same system configured for a same separation of isobutane between the second column side stream and the second column bottoms stream except wherein the second column pressure is not within about 10% of the first column pressure.

In a sixty fourth aspect, a system (of treating a polymerization reactor effluent, the system) comprises: one or more polymerization reactors configured to produce a polymerization reactor effluent stream; flash apparatus configured for flashing the polymerization reactor effluent stream to form a flash gas stream; a first column configured to separate the flash gas stream into a first column overhead stream, a first column side stream, and a first column bottoms stream; a liquid/vapor separator configured for separating the first column overhead stream into a gas stream and a liquid stream; and a second column configured to receive a feed comprising the gas stream and at least a portion of the liquid stream and separate the feed to produce a second column overhead stream, a second column side stream, and a second column bottoms stream, wherein the second column is operating at a second column pressure, and wherein the first column is operating at a first column pressure, wherein the second column pressure is within about 10% of the first column pressure.

In a sixty fifth aspect, a system (of treating a polymerization reactor effluent, the system) comprises: one or more polymerization reactors configured to produce a polymerization reactor effluent stream; flash apparatus configured for flashing the polymerization reactor effluent stream to form a flash gas stream; a first column configured to separate the flash gas stream into a first column overhead stream, a first column side stream, and a first column bottoms stream; a liquid/vapor separator configured for separating the first column overhead stream into a gas stream and a liquid stream; a second column configured to receive a feed comprising the gas stream and at least a portion of the liquid stream and separate the feed to produce a second column overhead stream, a second column side stream, and a second column bottoms stream, and a recycle path (e.g., a recycle line(s)) for recycling at least a portion of the second column side stream to at least one of the one or more polymerization reactors, wherein an amount of ethylene in the second column side stream is maximized, while a concentration of hydrogen in the second column side stream is below a tolerance of the one or more polymerization reactors (e.g., at less than about 10, 0.1, or 0.01 ppmw $H_2$).

While preferred aspects of the invention have been shown and described, modifications thereof can be made by one skilled in the art without departing from the teachings of this disclosure. The aspects described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention. The disclosures of all patents, patent applications, and publications cited herein are hereby incorporated by reference.

What is claimed is:

1. A method comprising:

recovering a polymerization reactor effluent stream from one or more polymerization reactors;

flashing the polymerization reactor effluent stream to form a flash gas stream;

separating, in a first column operated at a first column pressure, the flash gas stream into a first column overhead stream, a first column side stream, and a first column bottoms stream;

separating the first column overhead stream into a gas stream and a liquid stream; and introducing a feed comprising the gas stream and at least a portion of the liquid stream to a second column operated at a second column pressure, to produce a second column overhead stream, a second column side stream, and a second column bottoms stream, wherein the second column bottoms stream has a second column bottoms stream flow rate of isobutane and the second column side stream has a second column side stream flow rate of isobutane, wherein a total flow rate of isobutane comprises the second column bottoms stream flow rate and the second column side stream flow rate, and wherein the method comprises operating such that the second column bottoms stream flow rate comprises less than or equal to about 25 volume percent (vol %) of the total flow rate and the second column side stream flow rate comprises greater than or equal to about 75 vol % of the total flow rate; and wherein the method does not include compressing the first column overhead stream, the gas stream, or the at least the portion of the liquid stream prior to introducing the gas stream and the at least the portion of the liquid stream as the feed to the second column.

2. The method of claim 1, further comprising returning at least a portion of the first column side stream to at least one of the one or more polymerization reactors.

3. The method of claim 1 further comprising recycling at least a portion of the second column side stream to the one or more polymerization reactors.

4. The method of claim 1, wherein the second column bottoms stream is a substantially olefin-free isobutane stream comprising greater than or equal to about 95 weight percent (wt %) isobutane, less than or equal to about 50 ppmw olefins, less than or equal to about 0.1 ppmw hydrogen, or a combination thereof.

5. The method of claim 1 wherein the second column pressure is within 10% of the first column pressure.

6. The method of claim 1, wherein a reboiler duty of a reboiler associated with the second column is less than a reboiler duty of a reboiler associated with a second column in a same method except wherein the second column is not operated at a second column pressure that is within about 10% of the first column pressure, and wherein a diameter of the second column is less than a diameter of the second column utilized to provide a same separation in the same method.

7. The method of claim 1, comprising no preheating of the feed or components thereof between the second column and the first column.

8. The method of claim 1, wherein the second column side stream comprises less than or equal to about 0.1 ppmw hydrogen, less than or equal to about 10 weight percent (wt %) ethylene, greater than or equal to about 80 wt % isobutane, or a combination thereof.

9. The method of claim 1 further comprising maximizing an amount of ethylene in the second column side stream, while maintaining a concentration of hydrogen in the second column side stream below a tolerance of the one or more polymerization reactors, and recycling at least a portion of the second column side stream to at least one of the one or more polymerization reactors.

10. The method of claim 1 carried out with a system comprising:

the one or more polymerization reactors configured to produce the polymerization reactor effluent stream;

a flash apparatus configured for flashing the polymerization reactor effluent stream to form the flash gas stream;

the first column configured to separate the flash gas stream into the first column overhead stream, the first column side stream, and the first column bottoms stream;

a liquid/vapor separator configured for separating the first column overhead stream into a the gas stream and the liquid stream; and the second column configured to receive the feed comprising the gas stream and at least a portion of the liquid stream and separate the feed to produce the second column overhead stream, the second column side stream, and the second column bottoms stream, wherein a second column bottoms outlet line is configured for the second column bottoms stream flow rate of isobutane and a second column side stream is configured for the second column side stream flow rate of isobutane, and wherein the system does not comprise a compressor between the first column and the second column.

11. The method of claim 10, configured for operation of the second column at a pressure within about 10% of a pressure at which the first column is operated.

12. The method of claim 10, wherein the second column bottoms stream is a substantially olefin-free isobutane stream comprising greater than or equal to about 85 weight percent (wt %) isobutane, less than or equal to about 1 wt % olefins, less than or equal to about 0.1 ppmw hydrogen, or a combination thereof.

13. The method of claim 10, wherein the second column is in operation at a second column pressure and the first column is in operation at a first column pressure, wherein the second column pressure is within about 10% of the first column pressure.

14. The method of claim 13 wherein a reboiler duty of a reboiler associated with the second column is less than a reboiler duty of a reboiler associated with a second column in a same method except wherein the second column is not operated at a second column pressure that is within about 10% of the first column pressure, and wherein a diameter of the second column is less than a diameter of the second column utilized to provide a same separation in the same system.

15. The method of claim 10, comprising no compressor for compressing of the first column overhead stream, the gas stream, or the at least the portion of the liquid stream prior to introduction of the gas stream and the at least the portion of the liquid stream in the feed to the second column.

16. The method of claim 10, comprising no preheater for preheating of the feed or components thereof between the second column and the first column.

17. The method of claim 10, wherein a liquid side draw stage of the second column is separated from a feed stage of the second column by more than 5 theoretical or actual stages, or by from about 3 to about 20 theoretical or actual stages, wherein the liquid side draw stage is a stage from which or tray from immediately above which the second column side stream is withdrawn, and wherein the feed stage is a stage to which or a tray immediately above which the feed is introduced to the second column.

18. The method of claim 1, wherein the bottoms stream flow rate comprises less than or equal to about 15 volume percent (vol. %) of the total flow rate and the side stream flow rate comprises greater than or equal to about 85 vol. % of the total flow rate.

19. The method of claim 1, wherein the first column pressure and the second column pressure are in a range of from about 120 to 140 psig.

20. A method comprising:

recovering a polymerization reactor effluent stream from one or more polymerization reactors;

flashing the polymerization reactor effluent stream to form a flash gas stream;

separating, in a first column operated at a first column pressure, the flash gas stream into a first column overhead stream, a first column side stream, and a first column bottoms stream;

separating the first column overhead stream into a gas stream and a liquid stream;

introducing a feed comprising the gas stream and at least a portion of the liquid stream to a second column operate at a second column pressure to produce a second column overhead stream, a second column side stream, and a second column bottoms stream; and wherein the second column pressure is within about 10% of the first column pressure, and wherein the first column pressure and the second column pressure are in a range of from about 120 to 140 psig.

* * * * *